(12) United States Patent
Willson et al.

(10) Patent No.: US 12,214,298 B2
(45) Date of Patent: Feb. 4, 2025

(54) SYSTEMS AND METHOD FOR DETECTION OF ANALYTES IN HIGH VOLUMETRIC FLOW APPLICATIONS

(71) Applicant: University of Houston System, Houston, TX (US)

(72) Inventors: Richard C. Willson, Houston, TX (US); Ujwal Patil, Houston, TX (US); Binh V. Vu, Houston, TX (US); Ekaterini Kourentzi, Houston, TX (US); Mary Crum, Houston, TX (US)

(73) Assignee: University of Houston System, Houston, TX (US)

( * ) Notice: Subject to any disclaimer, the term of this patent is extended or adjusted under 35 U.S.C. 154(b) by 841 days.

(21) Appl. No.: 17/048,779

(22) PCT Filed: Apr. 17, 2019

(86) PCT No.: PCT/US2019/027965
§ 371 (c)(1),
(2) Date: Oct. 19, 2020

(87) PCT Pub. No.: WO2019/204508
PCT Pub. Date: Oct. 24, 2019

(65) Prior Publication Data
US 2021/0178290 A1 Jun. 17, 2021

Related U.S. Application Data

(60) Provisional application No. 62/659,461, filed on Apr. 18, 2018.

(51) Int. Cl.
*B01D 15/38* (2006.01)
*G01N 27/00* (2006.01)
*G01N 30/88* (2006.01)

(52) U.S. Cl.
CPC ....... *B01D 15/3885* (2013.01); *B01D 15/388* (2013.01); *G01N 27/00* (2013.01); *G01N 2030/8831* (2013.01)

(58) Field of Classification Search
CPC .................. B01D 15/3885; B01D 15/388; B01D 15/245; B01D 15/166; G01N 27/00; C12N 15/10
See application file for complete search history.

(56) References Cited

U.S. PATENT DOCUMENTS

| 5,149,661 A | 9/1992 | Gjerde et al. |
| 6,344,172 B1 | 2/2002 | Afeyan et al. |

(Continued)

FOREIGN PATENT DOCUMENTS

WO    WO2017/077086    5/2017

OTHER PUBLICATIONS

International Search Report and Written Opinion for PCT/US2019/027965 dated Jul. 15, 2019, 12 pages.

(Continued)

*Primary Examiner* — Chester T Barry
(74) *Attorney, Agent, or Firm* — Parker Highlander PLLC

(57) ABSTRACT

The present disclosure relates to the detection of analytes in high volumetric flow applications. Particular embodiments relate to the use of fluorescence polarization/anisotropy based for detection of analytes in a flow cell. In one testing format, an analyte of interest is probed with reagents containing fluorescent labeled recognition elements. When present in a sample or portion of a sample, the labeled analyte produces a shift in fluorescence polarization/anisotropy/intensity/lifetime as the output signal following the binding of the recognition elements to the analytes.

32 Claims, 15 Drawing Sheets
Specification includes a Sequence Listing.

(56) References Cited

U.S. PATENT DOCUMENTS

| | | | |
|---|---|---|---|
| 6,399,397 B1* | 6/2002 | Zarling | G01N 33/588 |
| | | | 436/805 |
| 2009/0142772 A1* | 6/2009 | Lau | G01N 33/54326 |
| | | | 435/7.1 |
| 2011/0100818 A1 | 5/2011 | Jackson et al. | |
| 2013/0273616 A1 | 10/2013 | Hicks et al. | |

OTHER PUBLICATIONS

International Preliminary Report on Patentability for PCT/US2019/027965 dated Oct. 20, 2020.

Zhang et al., "Immunoaffinity Column Cleanup with Liquid Chromatography Using Post-Solumn Bromination for Aflatoxins in Medicinal Herbs and Plant Extracts", Journal of Chromatographic Science, vol. 43, Jan. 2005, pp. 47-51.

* cited by examiner

1. Excitation light source
2. Condenser lens
3. Excitation filter
4. Unpolarized monochromatic light
5. Vertical polarizing filters
6. Lenses
7. Horizontal polarizing filter
8. Horizontal polarized emission light
9. Vertical polarized emission light
10. Emission filters
11. Focusing lenses
12. Detectors
13. Fluorescence polarization flow cell
14. Mixer
15. Tubing 1. Excitation light source
2. Condenser lens
3. Excitation filter
4. Unpolarized monochromatic light
5. Vertical polarizing filter
6. Lenses
7. Fluorescence polarization flow cell
8. Moving polarizing filter
9. Polarized emission light
10. Emission filter
11. Focusing lens
12. Detector
13. Mixer
14. Tubing

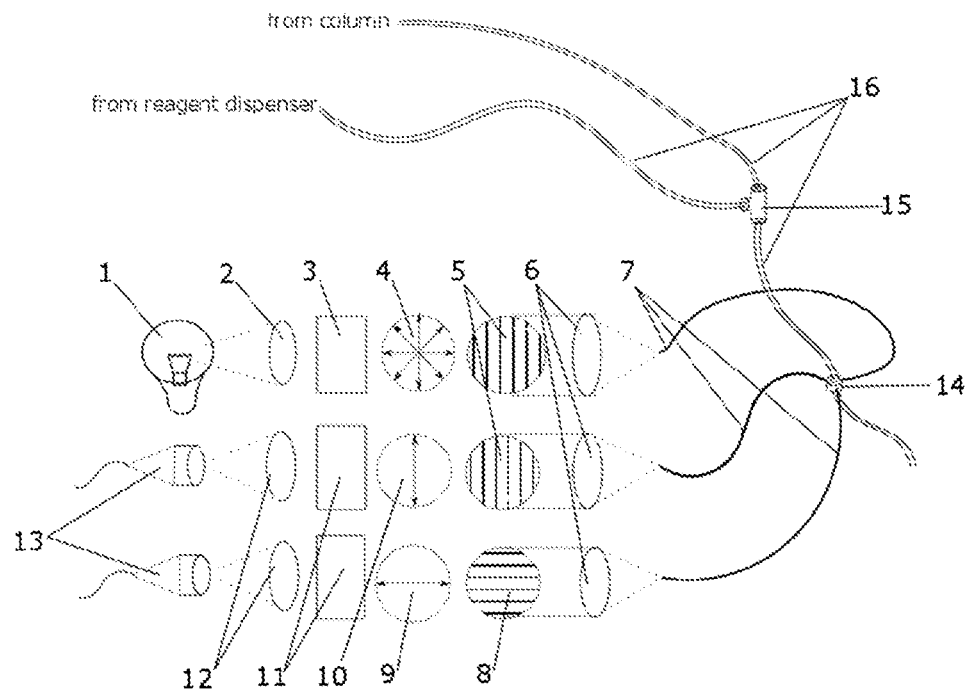

1. Excitation light source
2. Condenser lens
3. Excitation filter
4. Unpolarized monochromatic light
5. Vertical polarizing filters
6. Lenses
7. Polarization maintaining optical fibers
8. Horizontal polarizing filter
9. Horizontal polarized emission light
10. Vertical polarized emission light
11. Emission filters
12. Focusing lenses
13. Detectors
14. Fluorescence polarization flow cell
15. Mixer
16. Tubing

FIG. 6

1. Fluorophore
2. Recognition element
3. Flexible tethering molecule
4. Surface
5. Target molecule

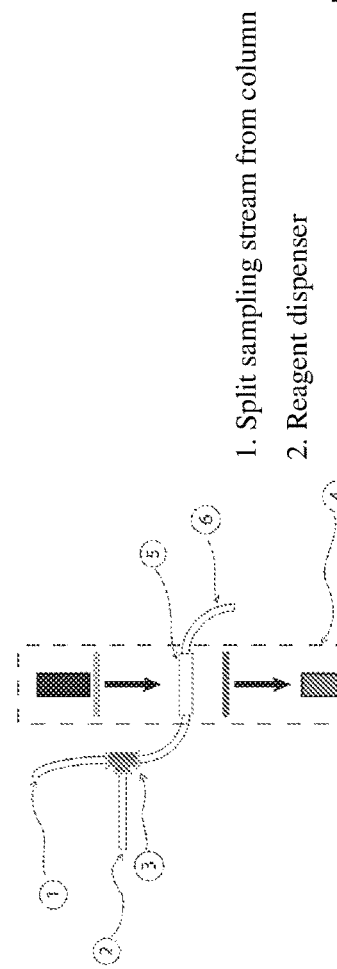
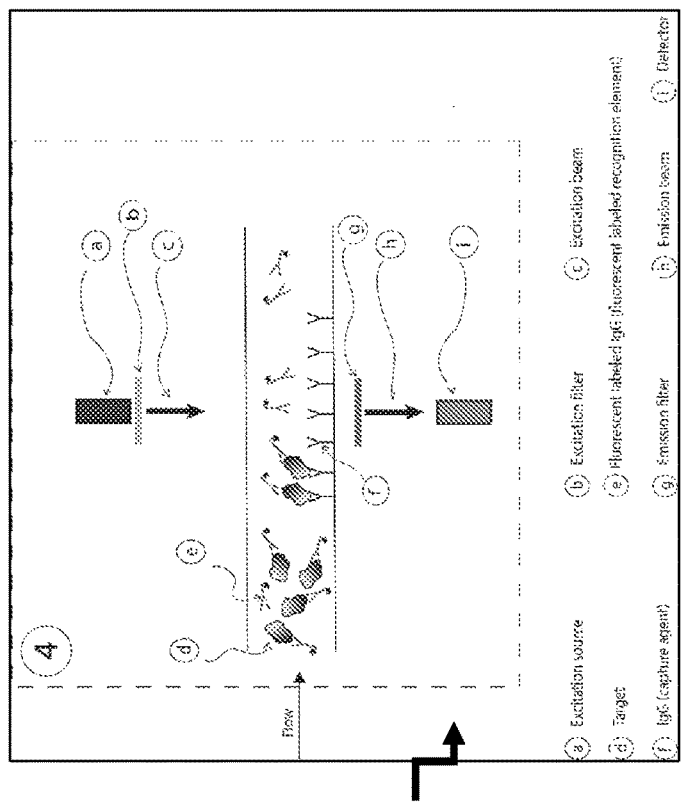
1. Split sampling stream from column
2. Reagent dispenser
3. T-mixer
4. Fluorescence detector assembly
5. Sensing area/fluorescence cell
6. fluorescence cell outlet
FIG. 8

SYSTEMS AND METHOD FOR DETECTION OF ANALYTES IN HIGH VOLUMETRIC FLOW APPLICATIONS

PRIORITY CLAIM

This application is a national phase application under 35 U.S.C. § 371 of International Application No. PCT/US2019/027965, filed Apr. 17, 2019, which claims benefit of priority to U.S. Provisional Application Ser. No. 62/659,461, filed Apr. 18, 2018, the entire contents of each of which are hereby incorporated by reference.

BACKGROUND

1. Field

The present disclosure relates to systems, methods, and kits for detection of analytes in high volumetric flow applications. Particular embodiments relate to fluorescence polarization/anisotropy based for detection of analytes in a flow cell. In a testing format, an analyte of interest is probed with reagents containing fluorescent labeled recognition elements to produce a shift in fluorescence polarization/anisotropy/intensity/lifetime as an output signal of the binding event.

2. Description of Related Art

Biopharmaceuticals (or biologics) are a class of drugs synthesized from biological sources that have a therapeutic effect. For example, monoclonal antibodies (mAbs) have become one of the major classes of biopharmaceuticals due to their high specificity for target molecules, thus reducing the risk of side effects to the patients. However, the cost of production of monoclonal antibodies is significantly higher than that of small molecule drugs due to their complexity and stringent purity regulatory requirements. The required high purity of monoclonal antibodies requires the culture fluid to go through many filtration and chromatography steps. The affinity chromatography step is usually the most expensive and the bottleneck of the mAb purification process. For mAb capture, Protein A coupled to agarose or other solid is the most common matrix. Protein A selectively binds antibodies in complex solutions, allowing impurities to flow through. During loading of a Protein A column, no antibody is present in the column effluent until the dynamic capacity of the column is reached and antibody begins flowing through the column without binding. The flow-through of antibody follows a breakthrough curve. Monitoring the breakthrough is very important to prevent precious antibody going to waste, and also to save time by letting the operator know when to stop loading, or to switch columns in a multi-column format. When loading purified antibody, the breakthrough curve can be monitored by UV absorbance. However, when loading cell culture fluid or cell lysate containing recombinant antibodies, antibody breakthrough cannot be measured using UV absorbance because host cell proteins, DNA, etc., in the flow-through impede UV detection of antibody breakthrough. Other methods have been used such as enzyme-linked immunosorbent assay (ELISA), surface plasmon resonance (SPR), proximity-based homogeneous assay, Raman spectroscopy, etc.; however, these technologies are generally too slow and/or costly or require too many reagents. Therefore, improved methods are needed.

SUMMARY

Thus, in accordance with the present disclosure, there is provided a method of detecting the presence of a target analyte comprising (a) contacting a sample or a separated portion of said sample with a reporter reagent that produces an optically or electromagnetically detectable signal in the presence of the target analyte; and (b) determining the presence of said target analyte in said sample or said separated portion of said sample by measuring the optically or electromagnetically detectable signal, thereby detecting the presence of said target analyte. The target analyte may be a protein, such as an antibody or antibody fragment, or may be a nucleic acid, a carbohydrate, a cell, a virus or a lipid.

The sample may be a first liquid stream derived from a separative process. The first liquid stream may be derived from a primary flow stream resulting from said separative process. The first liquid stream may comprise less than 1% of the volumetric flow rate of the primary flow stream. The primary flow stream may has a volumetric flow rate of more than about 1 mL per minute, more than about 50 mL per minute, or more than about 1 liter per minute. The primary flow stream and the liquid stream may be split by a liquid flow splitter in a T format, or repeatedly split with portions recycled into the main stream to achieve an effective very-unequal split.

The separative process may be chromatography, filtration/ultrafiltration or precipitation/$ZnCl_2$ precipitation. The reporter reagent may be introduced by mixing the sample prior to separation or be introduced by mixing a separated portion of said sample with said reagent. The separated portion of said sample may be mixed with a secondary liquid stream comprising the reporter reagent. The viscosity of the secondary liquid stream may be greater than about 2 centipoise. The reporter reagent may be introduced into the sample by dissolution or degradation of a solid matrix or transport through pores of a matrix, membrane or resin. The reporter reagent may alternatively be introduced into the separated portion of said sample by dissolution or degradation of a solid matrix or transport through pores of a matrix or resin.

Measuring may take place at a temperature of about 0 to 60° C., such as at a temperature of from about 0 to 30° C., or of from about 3 to 25° C. The pH of the primary flow stream is lower than about pH 4.2. The first liquid stream may be adjusted by titration or addition of a buffering species to a pH greater than 5.0. The mixture of the first liquid stream and the second liquid stream may be adjusted by titration or addition of a buffering species to a pH greater than 5.0. The reporter reagent may be associated with a particle, surface, or polymer. The sample maybe from a cell culture, or from a reactor vessel, such as a fermentation reactor or a precipitation reactor.

In another embodiment, there is provided a method of chromatographic purification of a target protein comprising (a) introducing a sample comprising a target protein into a chromatographic column; (b) capturing the target protein on a chromatographic column matrix in said chromatographic column; (c) eluting matrix-captured target protein by change of pH, change of salt concentration, or change of polarity or hydrophobicity of the liquid flowing through the column; (d) introducing a reporter reagent into a portion of the liquid leaving the chromatographic column, wherein the reporter agent binds the target protein; and (e) measuring the concentration of the target protein in the liquid leaving the chromatographic column by detecting the reporter agent.

The portion flow rate may be less than 2% of the volume flowing through the column, or at least 20 mL/min. Measuring may be performed within 10, 20, 60, 300, or 2000 seconds of emergence of the portion from the chromatographic column. The chromatographic column diameter may be at least 40 cm. Measuring may further be used to determine breakthrough during loading.

The method may further comprise redirecting liquid flow based on said measuring. The method may further comprise switching to a fresh chromatographic column based on said measuring. The method may further comprise switching collection volumes based on said measuring. Step (d) may be repeated at least 3, 10, or 25 times with the same chromatographic column or set of chromatographic columns. The volumetric productivity of said chromatographic column, as measured as product/packing volume/time, may increase by at least 5%, and step yield may decrease by not more than 5%, from switching strategies based on said measuring.

Exemplary embodiments of the present disclosure relate to systems, methods, and kits for measuring an analyte, including, for example, a monoclonal antibody in the effluent of a chromatography column being loaded with centrifuged, filtered, culture fluid.

Exemplary embodiments of the present disclosure include fluorescence polarization/anisotropy/intensity/lifetime for determining low-level monoclonal antibody from the effluent of the chromatography column. In one embodiment of the monitoring method, the effluent of chromatography column is tapped, and a small fraction is mixed with reagents containing fluorescent labeled recognition element to produce a shift in fluorescence polarization/anisotropy as the output signal of the binding event.

The recognition element can be proteins including but not limited to protein A, protein G, protein L, A, B, C, D, E and Z-domain from protein A, antibodies or fragments of antibody such as Fab, F(ab')2, Fab', single-chain variable fragment (scFv), dimeric single-chain variable fragment (di-scFv), single-domain antibody (sdAb), or nanobody against the analyte of interest, organic binding molecule or short peptide chain with the specific binding capability, synthetic cyclic peptide library of Fcγ-receptor mimic or proteins substantially similar to these. The recognition element can be nucleic acids with the specific binding capability to the target analyte such as DNA aptamer, or RNA aptamers. The recognition element can be artificially synthesized nucleic acids such as peptide nucleic acid (PNA), locked nucleic acid (LNA), glycol nucleic acid (GNA), or threose nucleic acid (TNA) with the sequence to specifically bind to the target analyte. The recognition element can be block copolymers synthesized specifically for the binding target analyte, or other organic molecules selected for binding to the target analyte, such as Protein A mimetics. The sequences for short peptides chain or cyclic with the specific binding capability are as follows but not limited to: TWKTSRISIF (SEQ ID NO: 1), FGRLVSSIRY (SEQ ID NO: 2), EPIHRSTLTALL (SEQ ID NO: 3), APAR (SEQ ID NO: 4), HWRGWV (SEQ ID NO: 5), HYFKFD (SEQ ID NO: 6), HWCitGWV (SEQ ID NO: 7), DAAG (SEQ ID NO: 8), cyclo([Nα-Ac)S(A)-RWHYFK-Lact-E] (SEQ ID NO: 9), cyclo([Nα-Ac)-Dap(A)-RWHYFK-Lact-E] (SEQ ID NO: 9), cyclo[Link-M-WFRHYK] (SEQ ID NO: 10), NKFRGKYK (SEQ ID NO: 11), NARKFYKG (SEQ ID NO: 12), FYWHCLDE (SEQ ID NO: 13), FYCHWALE (SEQ ID NO: 14), FYCHTIDE (SEQ ID NO: 15), RRGW (SEQ ID NO: 16), DCAWHLGELVWCT (SEQ ID NO: 17).

For the purposes of the present disclosure, a protein is "substantially similar to another protein if they are at least 80%, preferably at least about 90%, more preferably at least about 95% identical to each other in amino acid sequence and maintain or alter the biological activity of the unaltered protein. Amino acid substitutions which are conservative Substitutions unlikely to affect biological activity are considered identical for the purposes of this disclosure and include the following: Ala for Ser, Val for Ile, Asp for Glu, Thr for Ser, Ala for Gly, Ala for Thr, Ser for Asn, Ala for Val, Ser for Gly, Tyr for Phe, Ala for Pro, Lys for Arg, Asp for Asn, Leu for Ile, Leu for Val, Ala for Glu, Asp for Gly, and the reverse. (see, e.g., Neurath et al., 1979).

Detection can be by any optically or electromagnetically measurable method, including fluorescence intensity or polarization, fluorescence lifetime, fluorescence energy transfer, fluorescence correlation, fluorescence quenching, signals produced by enzymatic or other catalysts, Raman, absorbance, chemiluminescence, phosphorescence, infrared, NMR and EPR.

Labeled recognition agent can be introduced by mixing in a liquid solution of the recognition agent, by permeation across through pores (as of a membrane separating a liquid stream from a reservoir of recognition agent), by leaching or desorption or displacement from a solid containing the recognition agent, by dissolution or degradation of a matrix containing recognition agent, or by infusion of a stream from a disposable pump, particularly an osmotic or electrokinetic pump.

In one embodiment, for detection with fluorescence polarization, the recognition element can be labeled with fluorophores that have excited state lifetime greater than 0.2 ns, or greater than 2 ns. In one embodiment, multiple recognition elements labeled with different fluorophores that have distinguishable absorption and/or emission spectra are used to detect multiple target analytes or to detect a target analyte relative to another. The emission spectra can be partially overlapping in some cases. The detecting can comprise sequential measurement of fluorescence polarization of the target at one wavelength range and measurement of another target at another wavelength range. The concentration of the target analyte can be inferred by the ratio of the two measurements.

The fluorophore labeled recognition element can be mixed in with the sample in a flow setup at a fixed ratio and measured with a flow cell fluorescence polarization monitor downstream. In some embodiments, the mixer is built in the flow cell fluorescence polarimeter.

In an embodiment, a stream containing a target analyte such as an antibody is split into at least 2 streams and contacted with a particle, matrix, or surface which removes at least 10% of the analyte. A detection reagent is added to one or both streams, and an optical signal is measured in at least one stream. The difference in the signal between the two streams is used to determine the analyte concentration in the original stream.

In an embodiment, a liquid containing a target analyte such as an antibody is split into at least 2 volumes and one volume is contacted with a particle, matrix, or surface which removes at least 10% of the analyte. A detection reagent is added to one or both volumes, and an optical signal is measured in at least one volumes. The difference in the signal between the two volumes is used to determine the analyte concentration in the original liquid.

In an embodiment, the target analyte is a specific host cell protein or set of host cell proteins targeted by more than one molecular recognition element.

In an embodiment, the target analyte is a lipase, protease, or oxidoreductase derived from a mammalian cell expressing a pharmaceutically-active protein.

In an embodiment, the target analyte is a toxin.

In a favored embodiment, the molecular recognition element is less than 40,000 Da in molecular mass.

In a favored embodiment, the molecular recognition element is less than 2,000 Da in molecular mass.

In a favored embodiment, the molecular recognition element comprises a peptide linked to a polylysine structure, a cyclic peptide, a triazine, or an aromatic amine.

In an embodiment, contaminating nucleic acids are detected by contacting a stream containing a pharmacologically-active protein with a compound whose fluorescence intensity is increased by intercalation into nucleic acids.

In an embodiment, the fluorophore-labeled recognition element is tethered to the surface with a long linker such as polyethylene glycol (PEG), zwitterionic polymers, peptides, nucleic acids, to give the fluorophore-labeled recognition element rotational flexibility and low nonspecific binding. The fluorophores are selected to have compatible excited state lifetime for a desired responsivity and sensitivity to the presence of the analyte.

In another embodiment, the fluorophore-labeled recognition element is tethered to the tip of polarization-maintaining optical fiber with long linkers such as polyethylene glycol (PEG), zwitterionic polymers, peptides, nucleic acids, to give the fluorophore-labeled recognition element the rotational flexibility and low nonspecific binding. The fluorophores are selected to have compatible excited state lifetime for a desired responsivity and sensitivity to analyte concentration.

Detection by fluorescence intensity can use multiple molecular recognition agents recognizing the target, which interact by FRET or quenching, or allosteric reporters which change fluorescence intensity upon binding. The latter can be allosteric binding proteins labeled with fluors, or aptamers whose binding is detected by molecular beacon hybridization, optionally after a temperature or pH excursion. Fluorescence intensity also can be made responsive to the concentration of the analyte by making the location of a fluorescent label be dependent upon the presence the target analyte. For example, a fluorescent labeled molecular recognition agent can be removed from a flowing stream by permeation across a membrane with pores too small to allow passage of the complex between the recognition agent and a sufficiently large target (especially an antibody or virus), but large enough to allow passage of the uncomplexed recognition agent. Size-selective adsorbents such as ISRP or Capto resins can similarly be used to remove recognition agent in the absence of target.

The method is especially advantageous when applied to adsorptive separations in which the desired product is adsorbed, captured, retained, or delayed on the adsorbent. It is especially advantageous when applied during the loading of adsorbents, although monitoring of washing or elution also is a useful application. The method is especially advantageous when multiple (2-14) columns or other adsorbent volumes are used, when larger numbers of chromatographic cycles are used per fermentation/cell culture batch, when adsorbents are repeatedly reused for at least 30-100 cycles, and when adsorbent volumes are large (e.g., over 30-200 liters for batch and 5-30 liters for SMB), as in the manufacturing of commercial products. The method also is especially advantageous when adsorbents are loaded to a large fraction (65-100%) of their dynamic binding capacity. The method also is especially advantageous when affinity adsorbents are loaded to over 15-25 g product protein/L adsorbent, and when ion-exchange adsorbents are loaded to over 40-80 g product protein/L adsorbent, and when loading is stopped at a breakthrough of less than 5%. The method also is especially advantageous when adsorbents are loaded with a solution containing at least 2 g/L of the target protein, or operated at residence times below 5 minutes or operated at velocities of over 400 cm/h.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features, and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIG. 6. Flow fluorescence polarization monitoring with polarization-maintaining optical fibers FIG. 7. Fluorophore labeled recognition element tethered to surface of fluorescence polarization flow cell using flexible tethering molecule FIG. 8. Selective enrichment of the fluorescence signal FIG. 9. Selective enrichment of the fluorescence signal with a masking dye to reduce background FIG. 10. Monitoring the target protein in flow stream with TIRF FIG. 11. Shift of polarization of Fc-binding peptide, three-domain analog of Protein A and five-domain analog of Protein A upon mixing with IgG in batch mode.

DETAILED DESCRIPTION OF ILLUSTRATIVE EMBODIMENTS

Figure 1:
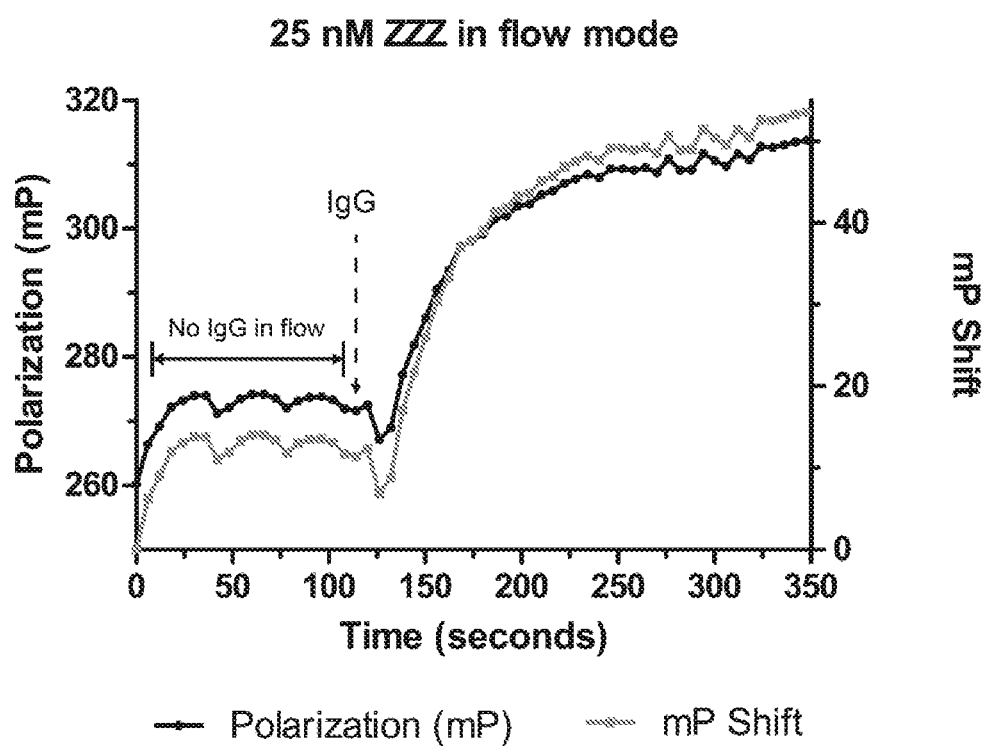
FIG. 1. Shift of polarization of a three-domain analog of Protein A upon mixing with IgG in flow mode. The three-domain analog of Protein A (0.5 mL/min) was initially mixed with a pure buffer stream (0.5 mL/min) followed by a stream (0.5 mL/min) containing IgG at 1 mg/mL.

As discussed above, monitoring breakthrough of biologics in chromatographic separation is difficult to measure due to the interference from other contaminating proteins in the flow-through. Most methods are too slow and/or require too many reagents and/or are exceedingly costly. Thus, the present disclosure describes improved methods that address this need with faster, simpler and less expensive methodologies.

The inventors provide here a new approach to monitoring breakthrough using fluorescence polarization/anisotropy in the flow cell to detect analytes in a complex mixture. In a testing format, an analyte of interest is probed with reagents containing fluorescent labeled recognition elements to produce a shift in polarization anisotropy as the output signal for a binding even, and in turn, for the presence of the analyte of interest. This approach is faster, more specific, and requires less reagent than the existing methods.

These and other aspects of the disclosure are described in detail below.

I. ANALYTES

The methods and compositions disclosed herein may be utilized to detect various analytes of interest from various sources. For instance, in some embodiments, analytes of interest include, without limitation, biopharmaceuticals generally, including monoclonal antibodies, antibody fragments, antibody conjugates and fusions, antibody-derived molecules including Fab, F(ab')2, Fab', single-chain variable fragment (scFv), dimeric single-chain variable fragment (di-scFv), single-domain antibody (sdAb), Fc fusions, bispecific antibodies, or nanobodies, PEGylated proteins, therapeutic nucleic acids, hormones and enzymes (such as insulin and tPA), growth factors and interleukins, human proteins, glycoproteins, lipoproteins, phosphoproteins, specific phosphorylated or acetylated variants of a protein.

Analytes to be detected or quantified may be isolated from various sources. For instance, in some embodiments, analytes may be isolated from Chinese hamster ovary (CHO) or other mammalian or insect cell cell cultures, yeast cell cultures, pharmaceutical production cultures, bacterial cultures, virus-infected cultures, microbial colonies, cell lysates, periplasmic lysates, and combinations thereof.

II. CHROMATOGRAPHY

Chromatography is a technique for the separation of a mixture. The mixture is dissolved in a fluid called the mobile phase, which carries it through a structure holding another material called the stationary phase. The various constituents of the mixture travel at different speeds, causing them to separate. The separation is based on differential partitioning between the mobile and stationary phases. Subtle or large differences in a compound's partition coefficient result in differential retention on the stationary phase and thus affect the separation.

Chromatography may be preparative or analytical. The purpose of preparative chromatography is to separate the components of a mixture for later use, and it is thus a form of purification. Analytical chromatography is normally applied to smaller amounts of material and is used for establishing the presence or measuring the relative proportions of analytes in a mixture. The two are not mutually exclusive.

Chromatography may be classified based on bed shape. This leads to the categories of column chromatography (e.g., HPLC), membrane, expanded-bed, and monolith chromatography and planar chromatography (e.g., TLC). Another category is displacement chromatography, where a molecule with a high affinity for the chromatography matrix (the displacer) competes effectively for binding sites, and thus displace all molecules with lesser affinities. Affinity chromatography operates based on selective non-covalent interactions between an analyte and specific molecules. It is often used in biochemistry in the purification of proteins conjugated or fused to tags, such as polyhistidine, but also can be applied to unmodified proteins by using affinity recognition agents. Other separation mechanisms include ion-exchange, size exclusion/gel permeation, reverse-phase chromatography, mixed-mode, and hydrophobic interaction chromatography. Chromatography and adsorption formats include two-dimensional chromatography, simulated moving-bed chromatography, rapid-switching multicolumn chromatography, gas chromatography, fast protein liquid chromatography, membrane adsorption, simulated moving bed chromatography, fluidized or magnetically-stabilized fluidized bed adsorption, carrousel continuous chromatography, moving bed chromatography, continuous chromatography, continuous multicolumn capture chromatography, "Accelerated seamless antibody purification", countercurrent chromatography, periodic countercurrent chromatography, chiral chromatography, and aqueous normal-chromatography.

High-Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in order of decreasing size, so long as the shape is relatively constant. Gel chromatography is well-suited for separating molecules of different size because separation is independent of all other factors such as pH, ionic strength, temperature, etc. There also is virtually no adsorption, less zone-spreading and the elution volume is related in a simple matter to molecular weight.

Affinity chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (by altering pH, ionic strength, metal ion or organic concentration, temperature, etc.).

A particular type of affinity chromatography useful in the purification of carbohydrate-containing compounds is lectin affinity chromatography. Lectins are a class of substances that bind to a variety of polysaccharides and glycoproteins. Lectins are usually coupled to agarose, e.g., by cyanogen bromide, though other supports such as acrylate or glass can be used. Concanavalin A coupled to Sepharose was the first material of this sort to be used and has been widely used in the isolation of polysaccharides and glycoproteins. Other lectins that have been used include lentil lectin, wheat germ agglutinin which has been useful in the purification of N-acetyl glucosaminyl residues and *Helix pomatia* lectin. Lectins themselves often are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to and capture lectins from lotus.

The matrix should be a substance that itself does not adsorb molecules to any significant extent and that has a broad range of chemical and physical stability. The ligand should be coupled in such a way as to not affect its binding properties. The ligand should also provide relatively tight binding, and it should be possible to elute the substance without destroying the sample or the ligand. One of the most common forms of affinity chromatography is immunoaffinity chromatography. Purification of most biological products involves an early capture stage using affinity column chromatography. Packed bed column chromatography has various advantages such as product concentration, simplicity in resin cleaning and reuse. These advantages are overshadowed by the batch mode of operation and suboptimal resin capacity utilization eventually causing productivity bottlenecks in purification. The optimum use of binding capacity is crucial for prohibitively expensive affinity resin like protein A. Continuous multicolumn chromatography is gaining popularity as a possible solution to underutilization of binding capacity esp. in early-stage clinical manufacturing. Continuous multicolumn chromatography usually involves some smaller columns connected in series instead of a single large column. These small columns are switched between the loading step and nonloading steps. The loading involves controlled breakthrough of the primary column onto the secondary column. The two modes for controlling loading are Time-based (static) or ultraviolet (UV) absorbance based (dynamic). Unlike the static mode, dynamic mode is tunable towards variations in product concentration in feed and inter-column performance. The current approaches for the dynamic control are based on AUV, a difference in UV signal between the column inlet and outlet. Use of AUV method is challenging as feed generally contains a plethora of UV absorbing interfering substances. An industry research group have previously demonstrated the use of multivariable wavelength detectors to control protein loading during continuous chromatography (Godawat et al., *Biotechnology J.* 7.12 (2012): 1496-1508). The recent report by another research group described an improved method for the dynamic control of protein loading. This method provides a solution for overcoming the difference in UV signal between impurities and proteins for the protein loadings that are 10-fold higher than previously reported in the literature (Chmielowski et al., *Journal of Chromatography A* 1526 (2017): 58-69). The generation of antibodies that would be suitable for use in accord with the present disclosure is discussed below.

III. DETECTION USING FLUORESCENCE POLARIZATION/ANISOTROPY INTENSITY

A. Molecular Recognition Element

Many analytical methods, including those of interest in the present disclosure, involve molecular recognition, and also transduction of the molecular recognition event into a usable signal. Molecular recognition refers to the affinity and specific tendency of particular chemical species to associate with one another, or with organisms or viruses displaying target chemical species. Well-known examples of molecular recognition include the hybridization of complementary DNA sequences into the famous double helix structure with very high affinity, and the recognition of foreign organisms or molecules in the blood stream by the antibodies produced by mammals, or selected analytes by deliberately selected monoclonal antibodies. There are many other examples of molecular recognition elements, including the recognition of carbohydrate molecules by lectins, nucleic acid recognition by proteins and nucleic acid analogs, the binding of antibodies by bacterial proteins, receptors and compliment proteins, the binding of analytes by antibody fragments, derivatives, and analogs, and a host of other examples. In a particular example, a protein A Z-domain is used as recognition element. DNA encoding the Z-domain was constructed with gene sequence:

```
                                    (SEQ ID NO: 18)
F: tcgataacaaattcaacaaagaacaacaaaacgcgttctatgagatc ttacatttacctaacttaaacgaagaacaacgaaacgccttcatccaaag tttaaaagatgacccaagccaaagcgctaacctttttagcagaagctaaaa agctaaatgatgctcaagcaccgaaag
```

-continued (SEQ ID NO: 19)
R: tcgactttcggtgcttgagcatcatttagcttttagcttctgctaa aaggttagcgctttggcttgggtcatcttttaaactttggatgaaggcgt ttcgttgttcttcgtttaagttaggtaaatgtaagatctcatagaacgcg ttttgttgttctttgttgaatttgtta In addition, appropriate restriction enzyme sites were introduced, and the resulting gene is cloned into suitable expression plasmids. The plasmids containing the gene of interests was transformed into BL21 cells and induced with IPTG, to express one copy of Z domain with or without a C-terminal cysteine. For the construction of multiple repeats of Z domain, the above described DNA plasmid of one Z domain is digested with suitable restrictions enzymes and dephosphorylated using Shrimp Alkaline Phosphatase (rSAP). The phosphorylated dsDNA Z ultramer is then ligated to the digested plasmid. Once ligated, the new plasmid will express two fused Z domains (ZZ). Additional Z domains sequences can be added using the same procedure as two copies protocol until the desired number of fused Z domains is reached. In some embodiments, label elements used in the methods of the present disclosure may also be associated with various molecular recognition elements. In some embodiments, the molecular recognition elements may be part of, associated with, or attached to labels. In some embodiments, molecular recognition elements can include, without limitation, antibody, antibody fragment, antibody analog, affibody, camelid or shark antibody analog, nucleic acid, carbohydrate, aptamer, ligand, chelators, peptide nucleic acid, locked nucleic acid, backbone-modified nucleic acid, DARPin, molecularly imprinted polymers, lectin, padlock probe, substrate, receptor, viral protein, mixed, cDNA, metal chelate, boronate, peptide, enzyme substrate, cell, tissue, microorganism, yeast, bacterium, parasite, protozoan, virus, antigen, hapten, biotin, hormone, drug, anti-RNA/DNA hybrid antibody, Protein A, L or G mimetics, mutS, anti-DNA antibody, anti-methylation antibody, or an anti-phosphorylation site antibody.

In particular, the present disclosure involves the use of fluorophores. A property of fluorophores is the fluorescence polarization signal when excited by polarized light of a suitable wavelength, thereby enabling the fluorescence polarization measurement to be made. Generally, the fluorophores used in the assay provided by the present disclosure are conjugated to the recognition element. Upon binding to the target analyte, the fluorescence polarization response of the fluorescent-labeled recognition element is shifted from low fluorescence polarization to high fluorescence polarization. Suitable fluorophores for use in the disclosure include, for example, fluorescein and its derivatives, TAMRA dye, Alexa Fluor dyes, boron-dipyrromethene (BODIPY) dyes, metal complex dyes (europium chelates, rhenium chelates, other transition metal chelates) and many other commonly used fluorescent compounds that have fluorescence polarization response when excited by polarized light. The fluorophores in this disclosure typically have excited state lifetime greater than 0.2-1 ns. In some embodiments, multiple recognition elements labeled with different fluorophores that have distinguishable absorption and/or emission spectra are used to detect multiple target analytes or to detect a target analyte relative to the other. The emission spectra can be partially overlapping in some cases. The detecting can comprise sequential measurement of fluorescence polarization of the target at one wavelength and measurement of another target at another wavelength. The concentration of the target analyte can be inferred by the ratio of the two measurements.

B. Fluorescence Polarization

Figure 3:
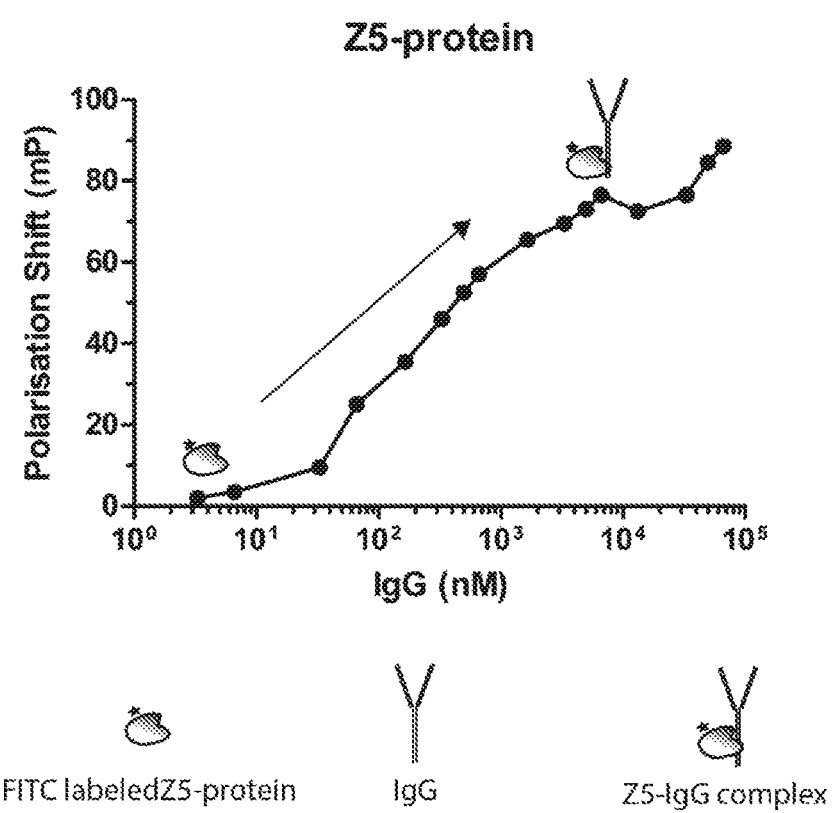
FIG. 3. Shift of polarization of a five-domain analog of Protein A in presence of increasing amount of human IgG in static mode.

Fluorescence polarization is based on the phenomenon that when a fluorescent molecule is excited with plane-polarized light, the polarization of the emitted light is dependent on its mobility. The emitted light from a small fluorescent molecule is largely depolarized because molecules tumble rapidly in solution during the fluorescence excited state lifetime (the time between excitation and emission). However, if the fluorescent molecule is bound by a larger molecule its effective molecular volume is increased. The rotation of fluorescent molecule is slowed so that the emitted light is more in the same plane as the excitation energy. The bound and unbound fluorescent molecules each have an intrinsic polarization value: a high value for the bound state and a low value for the free state. The polarization value (P) is a weighted average of the two values, thus providing a direct measure of the fraction of tracer bound to receptor (FIG. 3).

Figure 4:
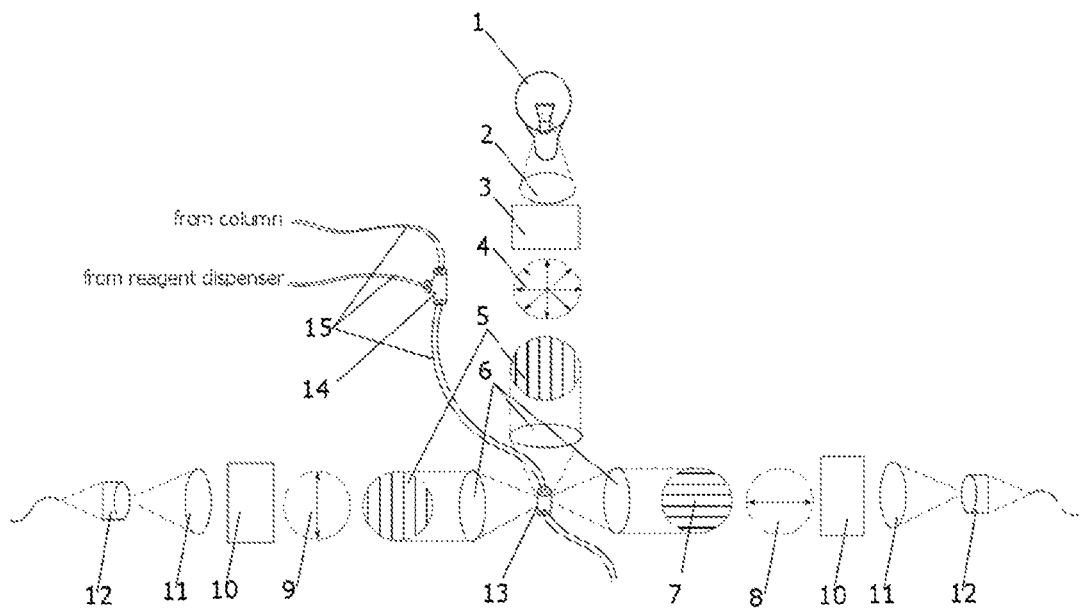
FIG. 4. T-format flow fluorescence polarization
Figure 5:
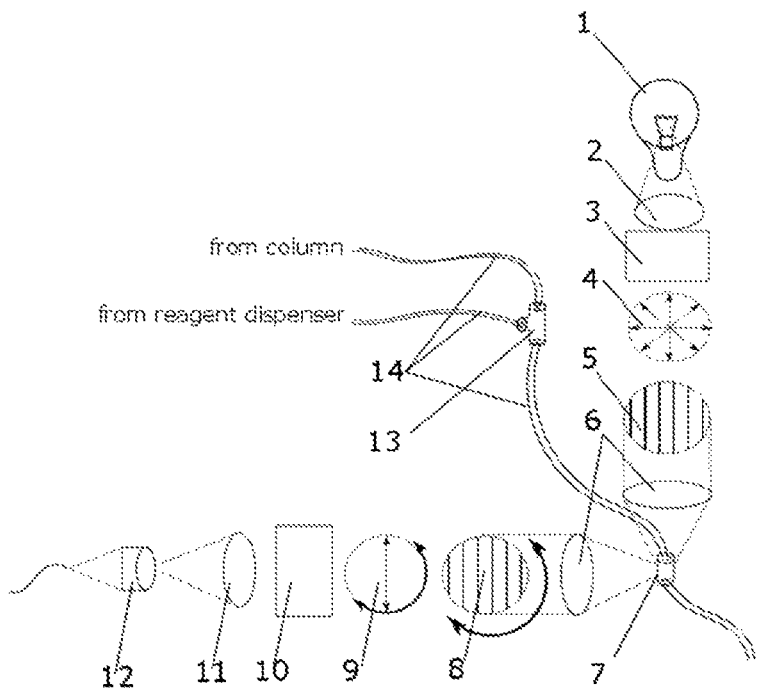
FIG. 5. L-format flow fluorescence polarization

In the present disclosure, fluorescence polarization can be measured with instrument setup in either T or L format. In a T-format (FIG. 4), the instrument has two detector arms symmetrically placed (typically at 90°) relative to the direction of the exciting light. Sample is excited by light polarized, e.g., parallel to the vertical axis. The intensities are measured along the two detector arms, detected through either parallel or perpendicular polarizers. In an L format (FIG. 5), the instrument has only one detector arm placed typically at 90° relative to the direction of the exciting light. The sample is excited by light polarized parallel to the vertical axis. The intensities were measured along the detector arm, which were detected through either parallel or perpendicular polarization by rotating the polarizer or optical modulation by 90°.

In an embodiment, to minimize the dead volume and consequently increase the response time, the fluorescence polarization instrument can be constructed from polarization-maintaining optical fiber (PMF or PM fiber), or photonic crystal fibers (PCF) (FIG. 6).

In particular embodiments, the detector is selected from the group consisting of a charged coupled device (CCD), avalanche diode, multi-pixel photon counter (MPPC), silicon photomultiplier (SiPMT), complementary metal-oxide-semiconductor (CMOS) sensor, scientific CMOS (sCMOS) sensor, photomultiplier tube (PMT), photodiode.

C. Fluorescent Label

The recognition elements or ligands used in fluorescence polarization assays are modified by the attachment of a fluorescent dye. The attachment of the dye molecule can be classified and rigid or flexible type. The presence of a linker between dye molecule and the recognition element is regarded as a flexible mode of attachment whereas the absence of a linker is regarded as a rigid attachment. The rigid attachment is preferred because it limits the ability of the dye to rotate independently of the overall motion of the ligand. The rotational correlation time of the recognition element should be shorter than the excited-state lifetimes the dye. The cyanine, fluorescein, Alexa Fluor 488, and BODIPY dyes have excited-state lifetimes ranging from 1 ns to 6 ns which are usually suitable for recognition elements with molecular weight less than or equal to 30,000 Da. Dansyl Chloride (20 ns) has been used in fluorescence polarization studies for bovine serum albumin (65,000 Da). Certain highly luminescent metal-ligand luminophores (MLLs) display highly polarized emission. The luminescence lifetimes for MLLs range from 100 ns to several microseconds. The longer luminescence lifetime of MLLs facilitates their use in polarization experiments with high molecular weight recognition elements. It has been previously reported that MLL like [Ru(2,2V-bipyridine)2(4,4V-dicarboxy-2,2V-bipyridine)]2+(RuBDc) can potentially be used in fluorescence polarization experiments with high-MW recognition elements like IgG (150,000 Da), concanavalin A (102,000 Da); and Ferritin (500,000 Da).

Fluorescent labeling of recognition elements can be performed using commercially available labeling chemistries for proteins, peptides, ligands, synthetic oligonucleotides. The selection reactive fluorescent or luminescent molecule is based on the availability of functional groups on the recognition element. The most common functional groups available of biomolecules are an amine, carboxyl, and thiol. In some cases, functional groups like aldehyde and/or ketones can be introduced on the biomolecules by treatment with mild oxidizing agents. The functional groups, e.g., azide can also be introduced into proteins or peptides by use of unnatural amino acids like azidonorleucine and azido phenylalanine. The azide functionality can be used to for fluorescent labeling using Azide-Alkyne Cycloaddition ("Click Chemistry"). For a typical fluorescent labeling reaction, the amount of recognition element is usually adjusted between 2-10 mg/mL in a suitable buffer depending on the solubility of the recognition element. The reactive fluorescent dye is dissolved in suitable solvent and then transferred to the recognition element solution. The reactive fluorescent dye is usually offered in 10-20-fold molar excess of the recognition element concentration. Following is an example of fluorescent labeling procedure of protein a Z-domain variant.

In this example, ZZZ-domain (>95% pure) is buffer exchanged into fresh 0.1M sodium carbonate buffer at pH 9.0. The final concentration of ZZZ-domain is adjusted to 5 mg/mL. 1 mg of Fluorescein isothiocyanate (FITC) is dissolved in 100 µL of anhydrous DMSO. The 100 µL of the FITC solution is transferred to 1 mL ZZZ-domain solution with constant mixing. The labeling reaction mixture is incubated on a shaker in the dark at room temperature for 90 mins. After completion of the incubation time, the labeling reaction is stopped by addition of 100 µL of 1.5 M hydroxylamine pH 8.5 to the reaction mixture. The reaction mixture is incubated further for 1 hour at room temperature. The unreacted FITC was removed using size exclusion chromatography using Superdex 75 GL (GE Healthcare). The fractions containing protein are pooled and affinity purified using IgG-Sepharose (GE Healthcare) column. The eluted fractions from the column are pooled, neutralized and concentrated.

In an embodiment, the molecular recognition element binds to the target in such a way that the fluorophore attached to the molecular recognition element is within 5 or 20 angstroms of an aromatic or cyclic residue in the target analyte.

In an embodiment, the molecular recognition element containing stream also serves a purpose of conditioning the sample solution. The conditioning allows altering of physical and/or chemical properties of the sample solution. The conditioning involves adjustment of pH and/or viscosity and/or temperature and/or conductivity and/or ionic composition of the sample solution prior to measurement.

IV. FLOW SPLITTER AND MIXER

A. Flow Splitters

Flow splitter is used to divide flow into two or more directions. The most common binary flow splitter divides the inlet stream to a primary outlet stream and a split stream. The primary outlet stream has a higher flow rate than a split stream. The ratio between the primary outlet stream and the split stream is regarded as a split ratio. The use of post-column flow splitter has been demonstrated previously in HPLC. Flow splitting is a way to reduce the flow rate down to a flow rate suitable for the desired detector. QuickSplit™ Flow Splitters (Analytical Scientific Instruments US, Inc.) allow accurate and reproducible flow splitting with split ratios ranging from 1:1 to 20,000:1. Depending on the mode of operation the split ratios in the splitters can be fixed or adjustable or automated. Following example illustrates the use of flow splitters to split a chromatography column effluent stream at high velocity.

A clarified harvested cell culture fluid containing recombinant IgG (4 g/L) is loaded on to Axichrom 100 column (packed with MabSelect SuRe™ pcc resin (GE Healthcare) with the packed bed volume of 0.79 Liter (bed height 10 cm). The flow velocity of 250 cm/h during loading is usually required to allow a residence time of 2.4 min. The said flow velocity translates to a flow rate of 19.6 L/h or 327 mL/min. A flow splitter attached to column outlet splits the outlet stream into primary and split streams. A flow splitter with a split ratio of 500:1 results in flow rate 326.35 mL/min in the primary stream and 0.65 mL/min in the split stream. The split stream is combined with reagents containing fluorescent labeled protein A Z domain in an active or passive mixer (such as T-connector) and the mixture flows to the flow cell fluorescence polarimeter. Alternatively, two flow splitters with lower split ratios are used in series to reduce the flow rate down to a flow rate suitable for the detector. This is achieved by using first flow splitter with a split ratio of 50:1 followed by second flow splitter with split ratio 10:1. In this case, split stream from the first flow splitter is split further by the second flow splitter. The resultant split stream from the second flow splitter is combined with reagents containing fluorescent labeled protein A Z domain in an active or passive mixer (such as T-connector) and the mixture flows to the flow cell fluorescence polarimeter.

In an embodiment, the splitting is performed in the pulse mode rather than continuous mode using a adjustable/programmable flow splitter. The pulse-split stream is combined with reagents containing fluorescent labeled molecular recognition element in an active or passive mixer (such as T-connector) and the mixture flows to the flow cell fluorescence polarimeter.

In an embodiment, the split sampling stream is generated using Hot-tapping/sampling. An adjustable pipe plug allows the sampling system to be inserted into high flow rate stream to the required length. The sampling assembly consists of an insertion rod, a welded pipe plug, and an sampling tip. The sampling tip can be either a quill, open, cap & core, or nozzle assembly type. The sampling is performed in the pulse mode or continuous mode. The sampling process can be driven by inherent pressure in high flow rate stream or assisted by a pump or both to minimize the delay time. The hot tapped sampling stream is combined with reagents containing fluorescent labeled molecular recognition element in an active or passive mixer (such as T-connector) and the mixture flows to the flow cell fluorescence polarimeter.

B. Mixer

A mixer unit enables mixing of 2 or more streams into a combined homogenous stream. The mixer units commercially available are either static or dynamic. The most common static mixer is a mixing Tee. A binary mixing Tee utilizes a specifically engineered internal geometry to efficiently mix two fluid streams into one combined stream. A mixing Tee can be accompanied by an inline mixer to reduce pulsation. Biocompatible static mixers with volumes that range from 0.5 µL to 15 mL are available from Analytical Scientific Instruments US, Inc. A dynamic mixer uses a magnetically coupled rotor for better mixing when compared to static mixers. The commercially available dynamic mixers usually have mixing volume ranging from 150 µL to 1 mL. The choice of mixer depends on dwell volume of the mixer, low mixing noise, and good mixing efficiency.

C. Kit

Certain embodiments may also comprise kits configured to perform methods such as those described herein.

A kit comprising a fluorophore-labeled recognition element. A kit can comprise a low or non-binding multiwall plate or cuvette. A kit can further comprise a fluorescence reader or fluorescence polarization analyzer.

All these elements will be put together in a single reaction kit compatible with the apparatus reason of the present invention, as long as they would not affect each other, and can be presented in an easily to use manner, for example, in powder or films or carried in a dry excipient. Furthermore, the whole kit should provide a standard reference in order to calibrate the apparatus. For further illustrate the present invention, the following examples are given.

Certain embodiments may also comprise kits configured to perform methods such as those described herein.

A kit comprising a fluorophore-labeled recognition element. A kit can comprise a low or non-binding multiwall plate, cuvette, or flow cell. A kit can further comprise a fluorescence reader or fluorescence polarization analyzer.

A kit can further comprise multiple fluorophore-labeled recognition elements with different excitation and emission spectra to monitor multiple targets or a single target with multiple ranges.

All these elements will be put together in a single reaction kit compatible with the apparatus reason of the present invention, as long as they would not affect each other, and can be presented in an easy to use manner, for example, in powder or films or carried in a dry excipient. Furthermore, the whole kit should provide a standard reference in order to calibrate the apparatus. For further illustrate the present invention, the following examples are given.

V. EXAMPLES

The following examples are included to further illustrate various aspects of the disclosure. It should be appreciated by those of skill in the art that the techniques disclosed in the examples which follow represent techniques and/or compositions discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1: Monitoring of Recombinant Antibody Breakthrough During Affinity Chromatography Using Fluorescent Labeled IgG Binding Protein Protein A is a 42 kDa protein originally found in *Staphylococcus aureus*. It has five homologous Ig-binding domains (A, B, C, D, and E). Protein A has the ability to bind immunoglobulins from many mammalian species, especially IgGs. It has strong binding affinity to the heavy chain within the Fc region of most immunoglobulins and also an affinity to some Fab regions. Its recombinant versions bind with great affinity only to the Fc region of IgG. Thus it is very useful in biopharmaceutical process.

In this example, a centrifuged CHO cell culture fluid containing recombinant IgG is passed through an affinity chromatography column (such as a protein A column) and the effluent of the chromatography column is monitored in real-time by tapping a small sampling stream which flows at high flow velocity to a polarization measurement device to minimize measurement delay time. Exemplary values include a capacity of 10 g/L at 1500 cm/h and 20 g/L at 600 cm/h. Protein A has a capacity at breakthrough of about 50 g/L.

The sampling stream is combined with reagents containing fluorescent labeled protein A Z domain in an active or passive mixer (such as T-connector) and the mixture flows to the flow cell fluorescence polarimeter. The polarimeter is an OLIS DM45 instrument with two (excitation, emission) single grating F/4.2 monochromators. Excitation is by a 150 Watt xenon arc lamp. For sensitive polarization measurements, a Photon Counting Module detector is used. Precise counting intervals of ten milliseconds are provided by a crystal-controlled counter/timer circuitry in the microcontroller. Standard spectral range is 280-630 nm.

The "1974 electro-optical method" described by Wampler and DeSa is used to measure L-format polarization. A photoelastic modulator (PEM) is used to vary the light's polarization orientation 50,000 times per second from parallel to perpendicular or left to right circularly polarized.

The amount of fluorescent-labeled protein A is optimized for desired sensitivity and response time. During the beginning of column loading, when the dynamic capacity of the column is not reached, the antibody is not present in the column effluent, and thus fluorescence polarization remains low. When the dynamic capacity of the column is reached, antibody begins flowing through the column without binding. The flowed-through antibody binds to the fluorescent labeled protein A to produce a shift in fluorescence polarization/anisotropy. The amount of shift in fluorescence polarization/anisotropy increases with the amount of antibody in the effluent stream (FIG. 1). When the shift in fluorescence polarization/anisotropy reaches a threshold, the loading of cell lysate can be stopped or diverted to a different column in a multi-column format to prevent precious antibody going to waste, and also to save processing time.

In other application of the technology, recombinant streptococcal protein G domain is used as an alternative. Protein G is an immunoglobulin binding protein expressed in Streptococcal bacteria similar to Protein A.

In other applications of the technology, recombinant protein A/G is used as an alternative. Protein A/G is a 50 kDa recombinant fusion protein that combines four Fc binding domains from Protein A and two from Protein G. Protein A/G has properties of Protein A and G, but the binding is less pH-dependent than that of Protein A. Protein A/G binds to all subclasses of human IgG, IgA, IgE, IgM, and IgD. In addition, Protein A/G also binds to all subclasses of mouse IgG but does not bind mouse IgA, IgM or serum albumin.

In other applications of the technology, protein L, anion-exchanger, cation-exchanger, metal chelate affinity, peptide ligand affinity such as Arg-Thr-Tyr, dye affinity, ligand affinity, camelid VHH ligand affinity, thiophilic affinity, mannose-binding protein affinity, or Streptococcal or another IgA-binding peptide affinity is used as an alternative.

Example 2: Monitoring of Recombinant Antibody Breakthrough During Affinity Chromatography Using Fluorescent Labeled Affibody Affibody molecules are small proteins engineered to bind to their target with high affinity. One of the earliest affibody molecules is Z-domain which was engineered from the B-domain in the immunoglobulin-binding region of staphylococcal protein A. The engineered Z-domain retained its affinity for the Fc part of the IgG antibody as the original B-domain but the affinity for the Fab region was removed. Affibody molecules are great for fluorescence polarization due to their low small size (about 6 kDa). Thus the fluorescent labeled affibody molecules have low intrinsic fluorescence polarization.

In this example, a cell lysate containing recombinant antibody fragment is passed through an affinity column (such as a protein A column) and the effluent of the chromatography column is monitored in real-time by tapping 0.1% of the column effluent. The sampling stream is combined with reagents containing fluorescent labeled Z-domain affibody released by an Alzet osmotic pump and flows to a flow cell fluorescence polarimeter. The rate of release of fluorescent labeled Z-domain affibody is optimized for desired sensitivity and response time. During the beginning of loading, when the dynamic capacity of the column is not reached, the antibody is not present in the column effluent. Thus fluorescence polarization remains low. When the dynamic capacity of the column is reached, antibody begins flowing through the column without binding. The flow-through antibody binds to the fluorescent labeled Z-domain affibody to produce an increase in fluorescence polarization/anisotropy. The amount of shift in fluorescence polarization/anisotropy is reflective of the amount of antibody in the effluent stream. When a shift in fluorescence polarization/anisotropy reaches a threshold, the loading of cell lysate can be stopped or diverted to a different column in a multi-column format to prevent precious antibody going to waste and also to save processing time.

In another example, the molecular recognition agent comprises multiple units of Z-domain. Since Z-domain is small, multiple units of Z-domain (up to 5 units) labeled with fluorescence still have low intrinsic fluorescence polarization, even without the expedient of using special fluorophores with long fluorescence lifetime.

Example 3: Monitoring of Monoclonal Antibody in Breakthrough During Continuous Affinity Chromatography on MabSelect SuRe pcc Using Fluorescent Labeled ZZZ-Domain MabSelect SuRe pcc (GE Healthcare) is most commonly used antibody purification resin for continuous chromatographic purification. The MabSelect SuRe ligand was developed by engineering one of the IgG-binding domains of protein A followed by its coupling to a high-flow agarose base matrix with an average bead size of 50 μm ultimately resulting in MabSelect SuRe pcc. MabSelect SuRe pcc provides a binding capacity of ~60 g IgG/L resin at 2.4 min residence time. The alkali-stabilized ligand allows cost-effective cleaning with 0.1-0.5 M NaOH over hundreds of purification cycles. During a typical continuous chromatography capture step, a clarified harvested cell culture fluid containing recombinant IgG 4.0 g/L is applied to columns at a flow velocity of 250 cm/h. The said flow velocity is selected to allow a residence time of 2.4 min for a column with a bed height of 10 cm. The Axichrom columns with internal diameters 50, 70, 100 mm the flow velocity of 250 cm/h corresponds to flow rate 81 mL/min, 160 mL/min and 327 mL/min respectively, for a given bed height of 10 cm. Axichrom 100 column packed with MabSelect SuRe™ pcc resin (GE Healthcare) with the packed bed volume of 0.79 Litre (bed height 10 cm). The flow velocity of 250 cm/h during loading is usually required to allow a residence time of 2.4 min. The said flow velocity translates to a flow rate of 19.6 L/h or 327 mL/min A flow splitter attached to column outlet splits the outlet stream into primary and split streams. A flow splitter with a split ratio of 500:1 results in flow rate 326.35 mL/min in the primary stream and 0.65 mL/min in the split stream. The split stream is combined with reagents containing fluorescent labeled protein A ZZZ-domain in an active or passive mixer (such as T-connector) and the mixture flows to the flow cell fluorescence polarimeter. In loading step of the affinity purification process, as the dynamic capacity of the column is reached, and antibody begins flowing through the column without binding. The flow-through of antibody binds to the fluorescent labeled ZZZ-domain to produce a shift in fluorescence polarization/anisotropy. The amount of shift in fluorescence polarization/anisotropy is proportional to the amount of antibody in the effluent stream. When the shift in fluorescence polarization/anisotropy reaches a threshold, the loading of feed can be diverted to the next column in a multi-column format.

In another example, in-line sampling T is used to directly sample the preparative column effluent.

Example 4: Monitoring of Monoclonal Antibody in Breakthrough During Continuous Affinity Chromatography Using Fluorescent Labeled Z5-Domain In this example, a clarified harvested cell culture fluid containing recombinant IgG 4.0 g/L is applied to columns at a flow velocity of 250 cm/h. The said flow velocity is selected to allow a residence time of 2.4 min for a column with a bed height of 10 cm. The Axichrom column with internal diameter of 50 mm the flow velocity of 250 cm/h corresponds to flow rate 81 mL/min, for a given bed height of 10 cm. Axichrom 50 column packed with MabSelect SuRe™ resin (GE Healthcare) with the packed bed volume of ~0.2 Litre (bed height 10 cm). The flow velocity of 250 cm/h during loading is usually required to allow a residence time of 2.4 min. The said flow velocity translates to a flow rate of 81 mL/min A flow splitter attached to column outlet splits the outlet stream into primary and split streams. A flow splitter with a split ratio of 100:1 results in flow rate 80.20 mL/min in the primary stream and 0.8 mL/min in the split stream. The split stream is combined with reagents containing fluorescent labeled ZS-domain (5 repeats of Z-domain from protein A) in an active or passive mixer (such as T-connector) and the mixture flows to the flow cell fluorescence polarimeter. In loading step of the affinity purification process, as the dynamic capacity of the column is reached, and antibody begins flowing through the column without binding. The flow-through of antibody binds to the fluorescent labeled ZS-domain to produce a shift in fluorescence polarization/anisotropy. The amount of shift in fluorescence polarization/anisotropy is proportional to the amount of antibody in the effluent stream. When the shift in fluorescence polarization/anisotropy reaches a threshold, the loading of feed can be diverted to the next column in a multi-column format.

Example 5: Monitoring of Monoclonal Antibody in Breakthrough During Continuous Affinity Chromatography Using Fluorescent Labeled Z5-Domain In this example, a clarified harvested cell culture fluid containing recombinant IgG 2.0 g/L is applied to a column at a flow velocity of 300 cm/h. The HiScale 16 column with internal diameter of 16 mm the flow velocity of 300 cm/h corresponds to flow rate ~10 mL/min, for a given bed height of 20 cm. HiScale 16 column is packed with MabSelect SuRe™ resin (GE Healthcare) with the packed bed volume of ~40 mL (bed height 20 cm). The flow velocity of 300 cm/h during loading is usually required to allow a residence time of 4 min. A flow splitter attached to column outlet splits the outlet stream into primary and split streams. A flow splitter with a split ratio of 20:1 results in flow rate 9.52 mL/min in the primary stream and 0.48 mL/min in the split stream. The split stream is combined with reagents containing fluorescent labeled ZS-domain (5 repeats of Z-domain from protein A) in an active or passive mixer (such as T-connector) and the mixture flows to the flow cell fluorescence polarimeter. In loading step of the affinity purification process, as the dynamic capacity of the column is reached, and antibody begins flowing through the column without binding. The flow-through of antibody binds to the fluorescent labeled ZS-domain to produce a shift in fluorescence polarization/anisotropy. The amount of shift in fluorescence polarization/anisotropy is proportional to the amount of antibody in the effluent stream. When the shift in fluorescence polarization/anisotropy reaches a threshold, the loading of feed can be diverted to the next column in a multi-column format.

Example 6: Monitoring of Recombinant Antibody Breakthrough During Affinity Chromatography Using Tethered Fluorescent Labeled Recognition Element Continuous adding fluorescent labeled recognition element such as antibody fragment, aptamer, and nanobody, etc., to the sampling stream can be costly in some applications Immobilization of the fluorescent-labeled recognition element to the surface would solve this problem. However, fluorescence polarization method would not be possible with immobilization due to the restriction in the molecular rotation. Using long fluorescence lifetime fluorophore and long flexible linker to tether the fluorescent labeled recognition element to the surface can enable measurement with fluorescence polarization method.

Figure 7:
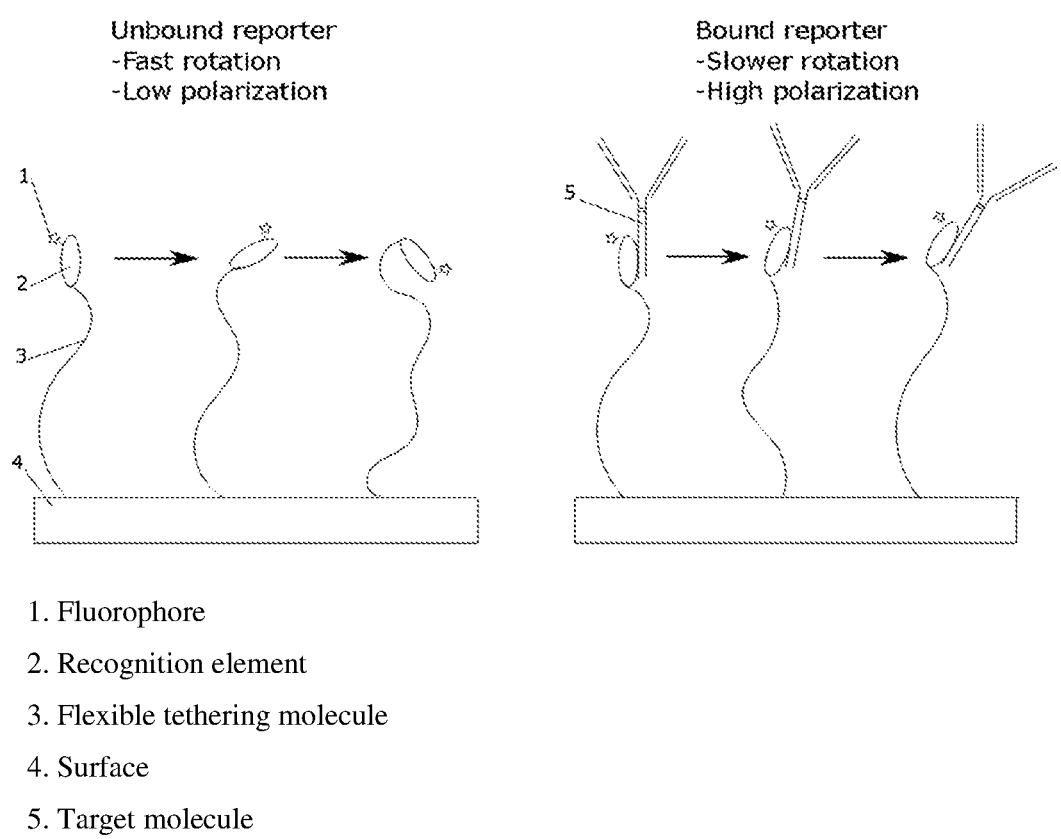

In this example, the cell lysate is passed through the affinity column and the effluent of chromatography column is monitored in real-time by tapping a small sampling stream at high flow velocity to minimize measurement delay time. The sampling stream is flow to the flow cell fluorescence polarimeter containing fluorescent labeled recognition element such as antibody, aptamer and nanobody, etc., that is tethered to the sensing surface with long linker such as polyethylene glycol (PEG), zwitterionic polymers, peptides, nucleic acids, to give the fluorophore-labeled recognition element the rotational flexibility and low nonspecific binding (FIG. 7). The fluorophore is selected with proper excited state lifetime that when excited by polarized light, the emission light of fluorophore-labeled recognition element to be depolarized light when free and polarized when bound to the antibody, or it is selected to change fluorescence intensity or lifetime when bound to the antibody. In loading step of the affinity purification process, the dynamic capacity of the column is reached, and antibody begins flowing through the column without binding. The flow-through of antibody binds to the tethered fluorescent labeled recognition element to produce shift in fluorescence polarization/anisotropy. The amount of shift in fluorescence polarization/anisotropy is proportional to the amount of antibody in the effluent stream. When the shift in fluorescence polarization/anisotropy reaches a threshold, the loading of cell lysate can be stopped or diverted to a different column in a multi-column format.

In another example, fluorescent labeled recognition element such as protein A Z domain tethered to the sensing surface with a poly-EK linker. This tether consists of repeated E (glutamic acid) and K(lysine) units, i.e., EK units to achieve the desired length of the tether. The polyEK tether is introduced biosynthetically by fusing the polyEK coding gene to the gene responsible for Z-domain. The available end on the polyEK tether can then be anchored to the sensing surface by use of covalent or non-covalent coupling methods.

Example 7: Monitoring of Monoclonal Antibody in Breakthrough During Continuous Affinity Chromatography Using Tethered Fluorescent Labeled Z3-Domain In this example, a clarified harvested cell culture fluid containing recombinant IgG 10.0 g/L is applied to a column at a flow velocity of 300 cm/h. The Axichrom 600 column with internal diameter of 600 mm, the flow velocity of 300 cm/h, corresponds to flow rate ~14.1 L/min, for a given bed height of 10 cm. Axichrom 600 column is packed with MabSelect SuRe™ resin (GE Healthcare) with the packed bed volume of ~28 L (bed height 10 cm). The flow velocity of 300 cm/h during loading is usually required to allow a residence time of 2 min. Two flow splitters are used in series to reduce the flow rate down to a flow rate suitable for the detector. This is achieved by using first flow splitter with a split ratio of 500:1 followed by second flow splitter with split ratio 50:1. In this case, the first flow splitter splits the inlet stream in two streams with flow rates ~14071.86 mL/min and 28.14 mL/min. 28.14 mL/min stream is split further by the second flow splitter in two streams with flow rates 27.59 mL/min and 0.55 mL/min. The resultant stream with flow rate 0.55 mL/min from the second flow splitter flows to the flow cell fluorescence polarimeter containing fluorescent labeled protein A Z3 domain that is tethered to the sensing surface with long linker such as zwitterionic peptides to give the fluorophore-labeled recognition element the rotational flexibility and low nonspecific binding (FIG. 7). The fluorophore is selected with proper excited state lifetime that when excited by polarized light, the emission light of fluorophore-labeled Z3 domain to be depolarized light when free and polarized when bound to the antibody, or it is selected to change fluorescence intensity or lifetime when bound to the antibody. In loading step of the affinity purification process, as the dynamic capacity of the column is reached, and antibody begins flowing through the column without binding. The flow-through of antibody binds to the tethered fluorescent-labeled Z3 domain to produce shift in fluorescence polarization/anisotropy. The amount of shift in fluorescence polarization/anisotropy is proportional to the amount of antibody in the effluent stream. When the shift in fluorescence polarization/anisotropy reaches a threshold, the loading of feed can be stopped or diverted to the next column in a multi-column format.

Example 8: Monitoring of Recombinant Antibody Breakthrough During Affinity Chromatography Using Tethered Fluorescent Labeled Recognition Element to the Optical Fiber Tip In this example, the cell lysate is passed through the affinity column and the effluent of chromatography column is monitored in real-time by tapping a small sampling stream at high flow velocity to minimize measurement delay time. The sampling stream is probed with optical fiber functionalized with fluorescent-labeled recognition element such as antibody, aptamer and nanobody, etc., that is tethered to the tip of the polarization-maintaining optical fiber with long linker such as polyethylene glycol (PEG), zwitterionic polymers, peptides, nucleic acids, to give the fluorophore-labeled recognition element the rotational flexibility and low nonspecific binding (FIGS. 6-7). The fluorophore is selected with proper excited state lifetime that when excited by polarized light, the emission light of fluorophore-labeled recognition element to be depolarized light when free and polarized when bound to the antibody. When the dynamic capacity of the column is reached, antibody begins flowing through the column without binding. The flow-through of antibody binds to the tethered fluorescent labeled recognition element to produce a shift in fluorescence polarization/anisotropy. The amount of shift in fluorescence polarization/anisotropy is proportional to the amount of antibody in the effluent stream. When the shift in fluorescence polarization/anisotropy reaches a threshold, the loading of cell lysate can be stopped or diverted to a different column in a multi-column format.

Example 9: Monitoring of Recombinant Antibody Breakthrough During Affinity Chromatography on HiScreen MabSelect SuRe LX Using Tethered Fluorescent Labeled Aptamer to the Optical Fiber Tip In this example, a clarified harvested cell culture fluid containing recombinant IgG 5.0 g IL is applied to a column at a flow velocity of 300 cm/h. The HiScreen MabSelect SuRe LX column (GE Healthcare) with internal diameter of 0.77 mm the flow velocity of 150 cm/h corresponds to flow rate ~2 mL/min, for a given bed height of 10 cm. HiScreen MabSelect SuRe LX column with the packed bed volume of ~4.7 mL (bed height 10 cm). A flow splitter attached to column outlet splits the outlet stream into primary and split streams. A flow splitter with a split ratio of 5:1 results in flow rate 1 mL/min in the primary stream and 0.2 mL/min in the split stream. The split stream flows to the flow cell fluorescence polarimeter. The sampling stream is probed with optical fiber functionalized with fluorescent-labeled recognition element such as aptamer that is tethered to the tip of the polarization-maintaining optical fiber with a long linker such as polyethylene glycol (PEG) to give the fluorophore-labeled recognition element the rotational flexibility and low nonspecific binding (FIGS. 6-7). The fluorophore is selected with proper excited state lifetime that when excited by polarized light, the emission light of fluorophore-labeled aptamer to be depolarized light when free and polarized when bound to the antibody. When the dynamic capacity of the column is reached, antibody begins flowing through the column without binding. The flow-through of antibody binds to the tethered fluorescent labeled aptamer to produce a shift in fluorescence polarization/anisotropy. The amount of shift in fluorescence polarization/anisotropy is proportional to the amount of antibody in the effluent stream. When the shift in fluorescence polarization/anisotropy reaches a threshold, the loading of cell lysate can be stopped or diverted to a different column in a multi-column format.

Example 10: Monitoring of Monoclonal Antibody in Breakthrough During Continuous Affinity Chromatography Using Fluorescent Labeled Antigen In this example, a clarified harvested cell culture fluid containing recombinant IgG 30.0 g/L is applied to a column at a flow velocity of 300 cm/h. ReadyToProcess MabSelect SuRe column is packed with MabSelect SuRe™ resin (GE Healthcare) with the packed bed volume of ~2.5 L (bed height 20 cm). ReadyToProcess columns are pre-packed and pre-sanitized hence reduces the risk of product contamination and carryover. ReadyToProcess columns are designed single-use hence remove time-consuming steps, in turn increase production capacity. The ReadyToProcess MabSelect SuRe column with internal diameter of 126 mm the flow velocity of 300 cm/h corresponds to flow rate ~624 mL/min, for a given bed height of 20 cm. The flow velocity of 300 cm/h during loading is usually required to allow a residence time of 4 min. A flow splitter attached to column outlet splits the outlet stream into primary and split streams. A flow splitter with a split ratio of 750:1 results in flow rate 623.17 mL/min in the primary stream and 0.83 mL/min in the split stream. The split stream is combined with reagents containing fluorescent labeled antigen in an active or passive mixer (such as T-connector) and the mixture flows to the flow cell fluorescence polarimeter. In this case, the antigen is the moiety which is the intended target for monoclonal antibody being purified, e.g., Tumor Necrosis Factor-alpha (TNFα) is a target for infliximab, adalimumab, certolizumab pegol and golimumab. In loading step of the affinity purification process, as the dynamic capacity of the column is reached, and antibody begins flowing through the column without binding. The flow-through of antibody binds to the fluorescent labeled antigen to produce a shift in fluorescence polarization/anisotropy. The amount of shift in fluorescence polarization/anisotropy is proportional to the amount of antibody in the effluent stream. When the shift in fluorescence polarization/anisotropy reaches a threshold, the loading of feed can be diverted to the next column in a multi-column format.

Example 11: Monitoring of Insulin Breakthrough During Purification Chromatography Using Fluorescent Labeled Recognition Element In this example, the cell lysate is passed through the column and the effluent of chromatography column is monitored in real-time by tapping a small sampling stream at high flow velocity to minimize measurement delay time. The sampling stream is combined with reagents containing fluorescent labeled recognition element such as antibody fragment, aptamer and nanobody, etc., in an active or passive mixer (such as T-connector) and flow to the flow cell fluorescence polarimeter. When the dynamic capacity of the column is reached, insulin begins flowing through the column without binding. The flow-through insulin binds to the fluorescent labeled recognition element to produce a shift in fluorescence polarization/anisotropy. The amount of shift in fluorescence polarization/anisotropy is proportional to the amount of insulin in the effluent stream. When the shift in fluorescence polarization/anisotropy reaches a threshold, the loading of cell lysate can be stopped or diverted to a different column in a multi-column format to prevent precious insulin going to waste and also to save processing time.

Example 12: Monitoring of Recombinant Antibody Breakthrough During Affinity Chromatography Using Fluorescent Labeled Aptamer In this example, the cell lysate is passed through a column of immobilized cyclized protein comprising multiple domains of Protein A and the effluent of chromatography column is monitored in real-time by tapping a small sampling stream at high flow velocity to minimize measurement delay time. The sampling stream is combined with reagents containing fluorescent labeled DNA aptamer with the length of less than 100 nucleotides. The mixture of sample and fluorescent labeled DNA aptamer is mixed and run thru the flow cell fluorescence polarimeter. When the dynamic capacity of the column is reached, recombinant antibody begins flowing through the column without binding. The flow-through recombinant antibody binds to the fluorescent labeled DNA aptamer to produce a shift in fluorescence polarization/anisotropy. The amount of shift in fluorescence polarization/anisotropy is proportional to the amount of recombinant antibody in the effluent stream. When the shift in fluorescence polarization/anisotropy reaches a threshold, the loading of cell lysate can be stopped or diverted to a different column in a multi-column format.

In other applications of the technology, locked nucleic acid (LNA), a nucleic acid analogue containing one or more LNA nucleotide monomers with a bicyclic furanose unit locked in an RNA mimicking sugar conformation, can be an alternative to DNA or RNA aptamer. LNA oligonucleotides display unprecedented hybridization affinity toward complementary single-stranded RNA and complementary single- or double-stranded DNA and have been recently incorporated into biosensor applications.

In other applications of the technology, peptide nucleic acid (PNA) is used as an alternative DNA or RNA aptamers. PNA is an artificially synthesized polymer similar to DNA or RNA. However, PNA's backbone is composed of repeating N-(2-aminoethyl)-glycine units linked by peptide bonds.

Example 13: Monitoring of Recombinant Antibody Breakthrough During Affinity Chromatography Using Fluorescent Labeled Recognition Element in a Competitive Format In this example, the cell lysate is passed through the column and the effluent of chromatography column is monitored in real-time by tapping a small sampling stream at high flow velocity to minimize measurement delay time. The sampling stream is combined with reagents containing fluorescent labeled Fc fragment of IgG and protein G in an active or passive mixer (such as T-connector) and flow to the flow cell fluorescence polarimeter. When the dynamic capacity of the column is reached, antibody begins flowing through the column without binding. The flow-through antibody displaces the Fc fragment from protein G. The increase of free Fc fragment produces a shift in fluorescence polarization/anisotropy. The amount of shift in fluorescence polarization/anisotropy is proportional to the amount of antibody in the effluent stream. When the shift in fluorescence polarization/anisotropy reaches a threshold, the loading of cell lysate can be stopped or diverted to a different column in a multi-column format to prevent precious insulin going to waste and also to save processing time.

Example 14: Monitoring of Proteins in Retentate During Isolation of Soy Proteins by Ultrafiltration Using Fluorescent Labeled Recognition Element In this example, the defatted soy flour slurry is adjusted to alkaline pH then passed through an ultrafiltration device and the retentate is monitored in real-time by tapping a small sampling stream at high flow velocity. The solubilized protein can pass through the ultrafiltration membrane while the membrane rejects phytate and aluminum. The sampling stream is combined with reagents containing fluorescent labeled recognition element specific for internal tracer protein, in an active or passive mixer (such as T-connector) and flows to the flow cell fluorescence polarimeter. The amount of fluorescent-labeled recognition element is optimized for desired sensitivity and response time. During the beginning of ultrafiltration, the retentate is rich in protein content. Thus fluorescence polarization remains high. Eventually, as the ultrafiltration proceeds, the protein content in the retentate is depleted. The protein depleted retentate stream leads to shift in fluorescence polarization/anisotropy. The reduction in fluorescence polarization/anisotropy is proportional to the depleted amount of protein in the retentate stream. When the shift in fluorescence polarization/anisotropy is below a threshold, the ultrafiltration process can be stopped or replenished with fresh feed containing soy flour slurry to save processing time.

Example 15: Monitoring of Proteins in Retentate During Isolation of Total Enzymatic Hydrolysate of Whey Proteins by Ultrafiltration Using Fluorescent Labeled Recognition Element In this example, the proteinaceous substrate or whey solution containing proteolytic enzyme is passed through an ultrafiltration device and the retentate is monitored in real-time by tapping a small sampling stream at high flow velocity. The proteinaceous substrate and enzyme are retained by the ultrafiltration membrane while the hydrolysis products, the peptides, are removed as they are formed. The sampling stream is combined with reagents containing fluorescent labeled recognition element specific for the proteinaceous substrate, in an active or passive mixer (such as T-connector) and flows to the flow cell fluorescence polarimeter. The amount of fluorescent-labeled recognition element is optimized for desired sensitivity and response time. During the beginning of ultrafiltration, the retentate is rich in protein content, thus fluorescence polarization remains high. Eventually, as the ultrafiltration proceeds, the proteinaceous substrate in the retentate is hydrolyzed. The proteinaceous substrate depletion in retentate stream leads to shift in fluorescence polarization/anisotropy. The reduction in fluorescence polarization/anisotropy is proportional to the depleted amount of proteinaceous substrate in the retentate stream. When the shift in fluorescence polarization/anisotropy is below a threshold, the ultrafiltration process can be stopped or replenished with fresh feed containing proteinaceous substrate to save processing time.

Example 16: Monitoring of Proteins in Permeate During the Preparation of Colostrum Fraction by Ultrafiltration Using Fluorescent Labeled Recognition Element In this example, the defatted colostrum is passed through an ultrafiltration device and the permeate is monitored in real-time by tapping a small sampling stream at high flow velocity. The harmful endotoxins, virus particles, immunoglobulins are retained by the ultrafiltration membrane while the colostrum fraction having a low endotoxin, protein and immunoglobulin concentration in recovered in permeate. The sampling stream is combined with reagents containing fluorescent labeled recognition element specific for intact immunoglobulins or immunoglobulin fragments, in an active or passive mixer (such as T-connector) and flows to the flow cell fluorescence polarimeter. The amount of fluorescent-labeled recognition element is optimized for desired sensitivity and response time. During the process of ultrafiltration, when the permeate is free from immunoglobulins or immunoglobulin fragments, fluorescence polarization remains low. When the immunoglobulins or immunoglobulin fragments leak into permeate stream and bind to the fluorescent labeled recognition element to produce a shift in fluorescence polarization/anisotropy. The shift in fluorescence polarization/anisotropy is proportional to the amount of immunoglobulin or immunoglobulin fragment leaked into the permeate stream. When the shift in fluorescence polarization/anisotropy reaches a threshold, the ultrafiltration process can be stopped to save processing time and unintended contamination of the product.

Example 17: Monitoring of Oligomeric Tannins in Permeate During Ultrafiltration of Red Wines Using Fluorescent Labeled Recognition Element In this example, the red press wine is passed through an ultrafiltration device and the permeate is monitored in real-time by tapping a small sampling stream at high flow velocity. The oligomeric tannins are retained by the ultrafiltration membrane while the permeate was continuously removed as a product. The sampling stream is combined with reagents containing fluorescent labeled recognition element specific for oligomeric tannins, in an active or passive mixer (such as T-connector) and flows to the flow cell fluorescence polarimeter. The amount of fluorescent-labeled recognition element is optimized for desired sensitivity and response time. During the process of ultrafiltration, when the permeate is free from oligomeric tannins, fluorescence polarization remains low. When the oligomeric tannins leak into permeate stream, and bind to the fluorescent labeled recognition element to produce a shift in fluorescence polarization/anisotropy. The shift in fluorescence polarization/anisotropy is proportional to the amount and size of oligomeric tannins leaked into the permeate stream. When the shift in fluorescence polarization/anisotropy reaches a threshold, the ultrafiltration process can be stopped to save processing time and unintended contamination of the product.

Example 18: Monitoring Detachment of Enzyme from Active Catalytic Membranes Using Fluorescent Labeled Recognition Element In this example, the substrate solution is passed through an enzymatic membrane reactor and the retentate is monitored in real-time by tapping a small sampling stream at high flow velocity. An enzymatic membrane reactor is equipped with the catalytic active membrane. The active catalytic membranes are prepared by covalent or noncovalent attachment of the enzyme to the membrane. The substrate is retained by the membrane while the product containing permeate is continuously removed. The sampling stream is combined with reagents containing fluorescent labeled recognition element specific for the enzyme, in an active or passive mixer (such as T-connector) and flows to the flow cell fluorescence polarimeter. The amount of fluorescent-labeled recognition element is optimized for desired sensitivity and response time. During the process of membrane catalysis, when the retentate devoid of free enzyme, fluorescence polarization remains low. When the enzyme detaches from the membrane into the retentate stream, it binds to the fluorescent labeled recognition element to produce a shift in fluorescence polarization/anisotropy. The shift in fluorescence polarization/anisotropy is proportional to the amount of detached enzyme in the retentate stream. When the shift in fluorescence polarization/anisotropy reaches a threshold, the catalysis process can be stopped to operation at sub-optimal capacity.

Example 19: Monitoring BK Virus in Cases of Viruria Using Fluorescent Labeled BK Virus Antibody In this example, the urine solution is passed through urinary flow meter or kidney dialysis machine and the inlet stream is monitored in real-time by tapping a small sampling stream at high flow velocity. After early childhood exposure, BK virus remains latent in healthy individuals. In patients receiving immunosuppression therapy following a transplant, the BK virus reactivation could occur. The BK virus is often found the urinary excretion of such patients. The sampling stream is combined with reagents containing fluorescent labeled BK virus antibody, in an active or passive mixer (such as T-connector) and flows to the flow cell fluorescence polarimeter. The amount of fluorescent-labeled recognition element is optimized for desired sensitivity and response time. When the urine is devoid of BK virus, fluorescence polarization remains low. When the BK virus is present in urine, it binds to the fluorescent labeled antibody to produce a shift in fluorescence polarization/anisotropy. The shift in fluorescence polarization/anisotropy is proportional to the amount of BK virus in urine.

Example 20: Renal Tissue and Urinary Tract Proteins in the Human Urine During Space Flight In this example, the urine is sucked into a Urine Processor Assembly (UPA) using a tube equipped with a vacuum. The inlet stream to the UPA is monitored in real-time by tapping a small sampling stream at high flow velocity. The internal organs in the human body are acutely sensitive to changes in the biomechanical environment and prolonged exposure to microgravity causes bone demineralization, skeletal muscles to lose mass, and the loss of tissue. Both quantity and spectrum of urinary proteins may change and include proteins beyond the common spectrum of "physiologic proteinuria." In astronauts undergoing prolonged exposure microgravity, the disturbance of the urogenital system could occur. The various renal tissue and urinary tract proteins are often found in the urinary excretion of astronauts after space flights. The sampling stream is combined with reagents containing fluorescent labeled recognition element, e.g., antibody, affibody in an active or passive mixer (such as T-connector) and flows to the flow cell fluorescence polarimeter. The amount of fluorescent-labeled recognition element is optimized for desired sensitivity and response time. When the urine is devoid of the target tissue protein, fluorescence polarization remains low. When the tissue protein is present in urine, it binds to the fluorescent labeled antibody to produce a shift in fluorescence polarization/ anisotropy. The shift in fluorescence polarization/anisotropy is proportional to the amount of target tissue protein.

Example 21: Monitoring of Enzyme Breakthrough During Purification Chromatography Using Fluorescent Labeled Recognition Element Enzymes are typically more detectable and measurable than other biomolecules due to the detectability of their products. However, many enzymes do not produce detectable substrates. Fluorescent-labeled recognition element such as modified enzyme substrate, antibody fragment, aptamer and nanobody, etc., can be used to measure these enzymes. The fluorescent-labeled recognition element binds to the enzyme to produce a shift in fluorescence polarization/anisotropy. Enzymes can also be measured indirectly by monitoring the concentration of their products or substrates. The fluorescent-labeled recognition element can be designed to bind to enzyme products or substrates. The change in concentration of enzyme products or substrates shifts the fluorescence polarization/anisotropy.

In this example, the cell lysate containing precious recombinant enzyme is passed through the chromatography column, and the effluent of chromatography column is monitored in real-time by tapping a small sampling stream at high flow velocity to minimize measurement delay time. The sampling stream is combined with reagents containing fluorescent labeled recognition element such as modified enzyme substrate, antibody fragment, aptamer and nanobody, etc., in an active or passive mixer (such as T-connector) and flow to the flow cell fluorescence polarimeter. When the dynamic capacity of the column is reached, enzyme begins flowing through the column without binding. The flow-through enzyme binds to the fluorescent labeled recognition element to produce a shift in fluorescence polarization/anisotropy. The amount of shift in fluorescence polarization/anisotropy is proportional to the amount of enzyme in the effluent stream. When the shift in fluorescence polarization/anisotropy reaches a threshold, the loading of cell lysate can be stopped or diverted to a different column in a multi-column format to prevent precious enzyme going to waste and also to save processing time.

In another example, the fluorescent-labeled recognition element has the affinity to the product from enzymatic reaction catalyzed by the enzyme. The presence of the enzyme produces an increase in production of the enzymatic product which binds to the fluorescent labeled recognition element to produce a shift in fluorescence polarization/anisotropy.

In another example, the fluorescent-labeled recognition element has the affinity to the substrate of the enzymatic reaction catalyzed by the enzyme. The presence of the enzyme produces a decrease in the substrate concentration which shifts fluorescence polarization/anisotropy.

Example 22: Monitoring of Recombinant Adenovirus Breakthrough During Purification Chromatography Using Fluorescent Labeled Recognition Element Due to the rapid expanding in the field of gene therapy, the classical adenovirus production with ultracentrifugation on a CsCl gradient is replaced with more complex techniques based on column chromatography and membrane techniques to produce of high purity grade and up-scaled production suitable for human clinical applications.

In this example, the cell lysate containing recombinant adenovirus is passed through the chromatography column, and the effluent of chromatography column is monitored in real-time by tapping a small sampling stream at high flow velocity to minimize measurement delay time. The sampling stream is combined with reagents containing fluorescent labeled recognition element such as antibody fragment, aptamer and nanobody, etc., in an active or passive mixer (such as T-connector) and flow to the flow cell fluorescence polarimeter. When the dynamic capacity of the column is reached, recombinant adenovirus begins flowing through the column without binding. The flow-through recombinant adenovirus binds to the fluorescent labeled recognition element to produce a shift in fluorescence polarization/anisotropy. The amount of shift in fluorescence polarization/anisotropy is proportional to the amount of recombinant adenovirus in the effluent stream. When the shift in fluorescence polarization/anisotropy reaches a threshold, the loading of cell lysate can be stopped or diverted to a different column in a multi-column format to prevent precious recombinant adenovirus going to waste and also to save processing time.

Example 23: Monitoring of Lentiviral Vectors in Nanofiber Adsorbent Breakthrough During Purification Using Fluorescent Labeled Recognition Element Lentiviral vectors (LVs) are becoming a significant tool in the field of gene therapy. The purification process for LVs usually involves the use of ultrafiltration, tangential flow filtration and chromatography. Recently, electrospun polymeric nanofiber adsorbents have been reported as an alternative method for purification of proteins (FibroSelect, Puridify), viruses and other biomolecules. Nanofiber adsorbents provide a high surface area that allows for rapid convective flow.

In this example, the feed containing LVs is passed through a nanofiber adsorbent cartridge, and the outlet of the adsorbent cartridge is monitored in real-time by tapping a small sampling stream at high flow velocity. An adsorbent cartridge is packed with nanofiber adsorbent of varying bed heights. The nanofiber adsorbents are prepared by covalent or non-covalent attachment of ion exchange or affinity ligands. The LVs are retained by the nanofiber adsorbents while the outlet stream depleted in LVs is continuously monitored. The sampling stream is combined with reagents containing fluorescent labeled recognition, e.g. Fab fragment specific for the LVs, in an active or passive mixer (such as T-connector) and flows to the flow cell fluorescence polarimeter. The amount of fluorescent-labeled recognition element is optimized for desired sensitivity and response time. During the purification process, when the outlet stream is devoid of LVs, fluorescence polarization remains low. As the dynamic binding capacity of the nanofiber adsorbent is consumed, the unbound LVs in outlet stream binds to the fluorescent labeled recognition element to produce a shift in fluorescence polarization/anisotropy. The shift in fluorescence polarization/anisotropy is proportional to the amount of LVs in the outlet stream. When the shift in fluorescence polarization/anisotropy reaches a threshold, the purification process can be stopped, or the outlet stream can be diverted to fresh nanofiber adsorbent.

Example 24: Monitoring of Target Protein in a Flow Stream Using Fluorescent Labeled Recognition Element In this example, the fluorescence sensing cell is coated with capture element having specific affinity for the target protein. The coating of the capture element can be performed by using covalent or non-covalent coupling methods. A high velocity stream containing target of interest is split using a fixed or variable or automated flow splitter with split ratios ranging from 10:1 to 20000:1 The split sampling stream is combined with reagents containing fluorescent labeled recognition element which binds to a part of the target protein distinct from the part that binds to the capture element. The fluorescent-labeled recognition element is mixed with the sampling stream using an active or passive mixer (such as T-connector) or inline mixer and flows to the fluorescence sensing cell. The amount of fluorescent-labeled recognition element is optimized for desired sensitivity. When the sampling stream is devoid of the target, fluorescence remains low. As the amount of target in sampling stream increases, it binds to the fluorescent labeled recognition element. This complex, in turn, binds to capture element and is recorded as fluorescence signal (FIG. 8). The fluorescence signal intensity increases with the amount of target in the sampling stream.

Figure 9:
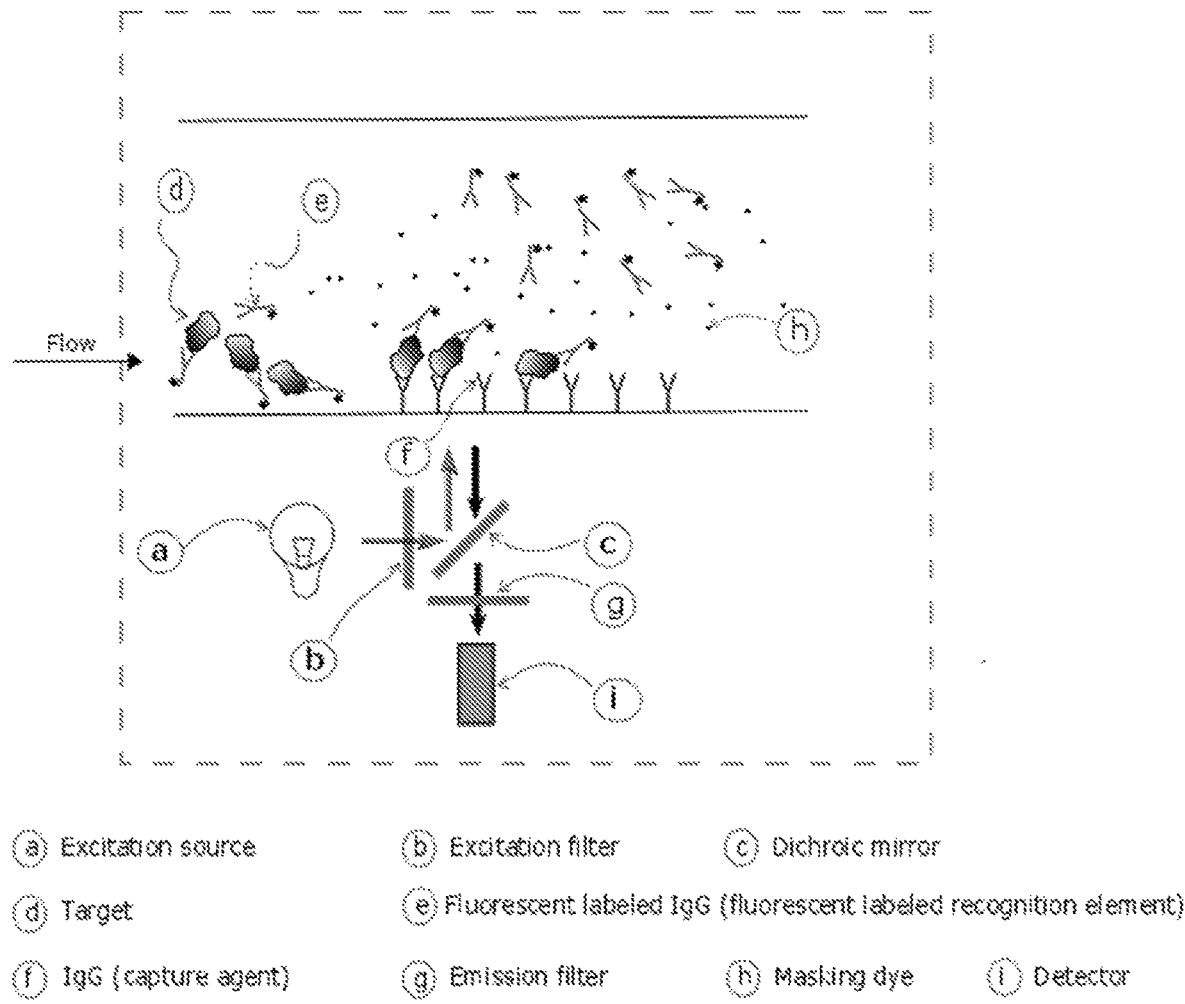

In another example, dye is added to as a component of the reagents. The dye is selected to have the light absorption overlapping the excitation and/or emission wavelengths of the fluorescent label. When the sampling stream is devoid of the target, front-face fluorescence signal remains low. The added dye blocks the excitation light and/or absorbs the emission light of uncaptured fluorescent label in the bulk volume above the sensing surface (FIG. 9). As the amount of target in sampling stream increases, it binds to the fluorescent labeled recognition element and is captured on the sensing surface, causing the front-face fluorescence signal to increase. The dye has minimal effect on the signal at the sensing surface. The fluorescence signal intensity is interpreted as the amount of target protein present.

Figure 10:
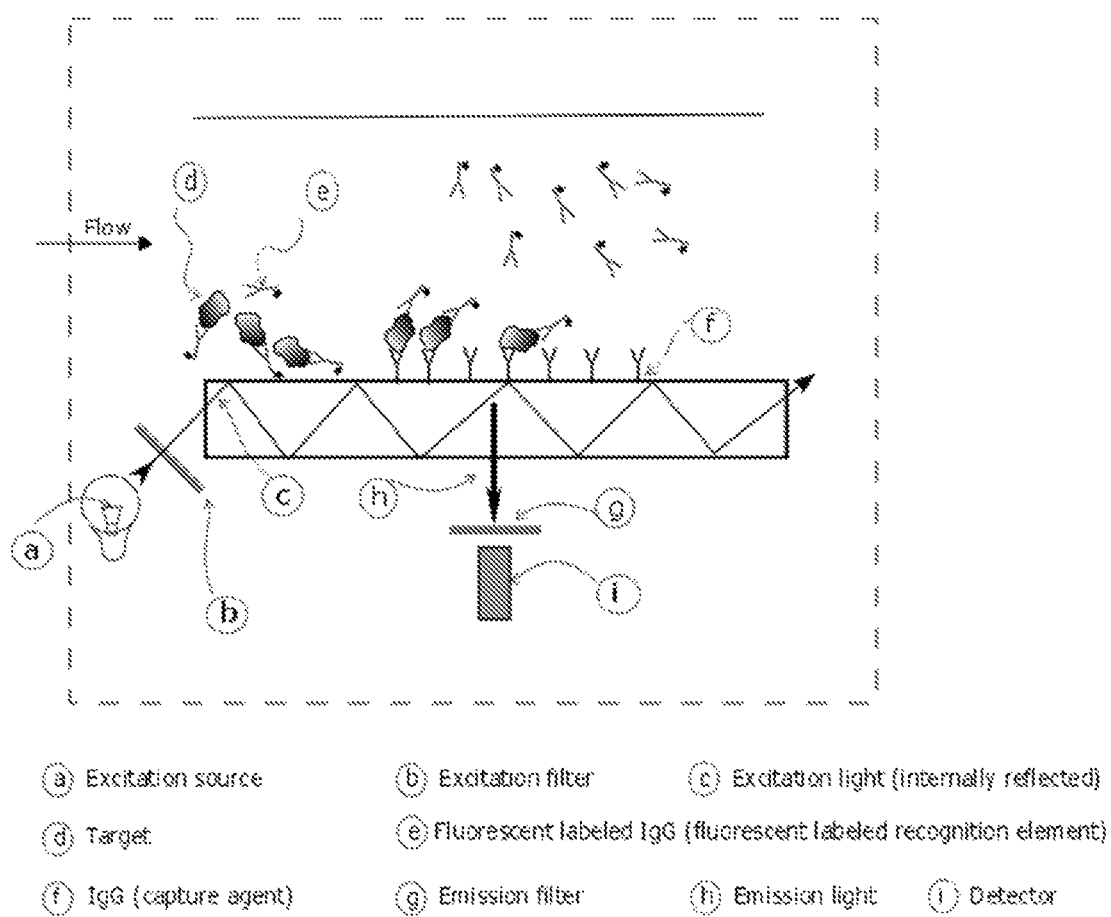
Figure 11:
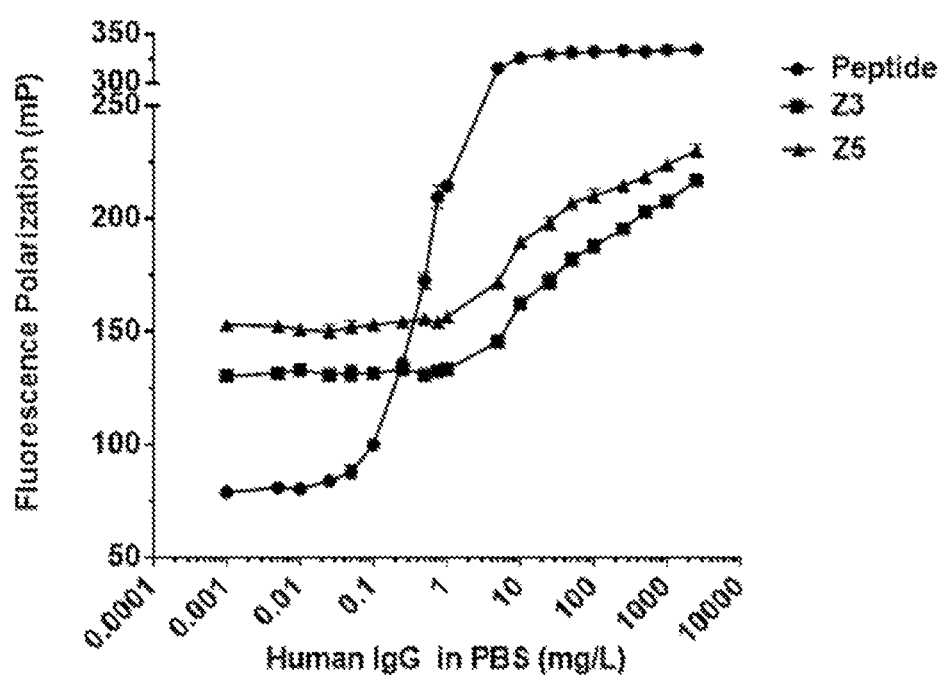
Figure 12:
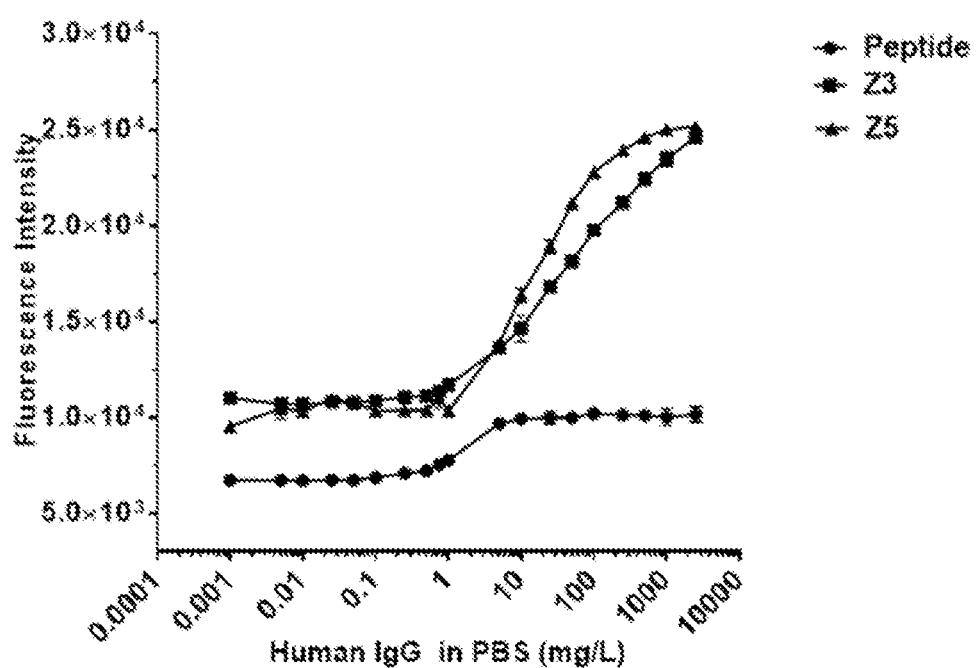
FIG. 12. Shift of fluorescence intensity of Fc-binding peptide, three-domain analog of Protein A and five-domain analog of Protein A upon mixing with IgG in batch mode FIG. 13. Shift of fluorescence polarization of Fc-binding peptide and three-domain analog of Protein A upon mixing with IgG in batch mode in cell culture fluid FIG. 14. Shift of fluorescence intensity of Fc-binding peptide and three-domain analog of Protein A upon mixing with IgG in batch mode in cell culture fluid FIGS. 15A-C.
Figure 13:
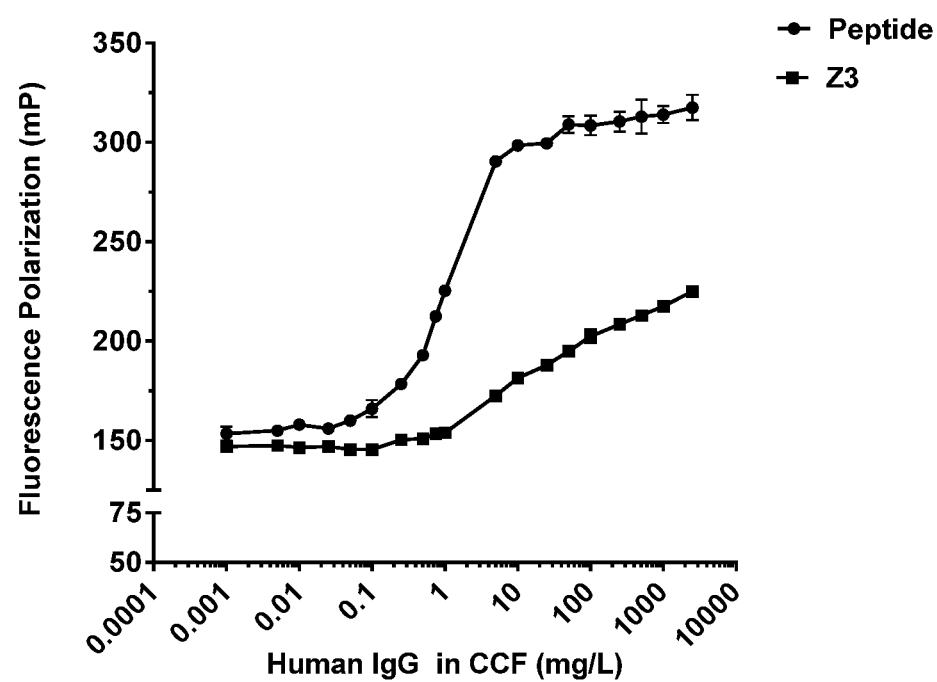
Figure 14:
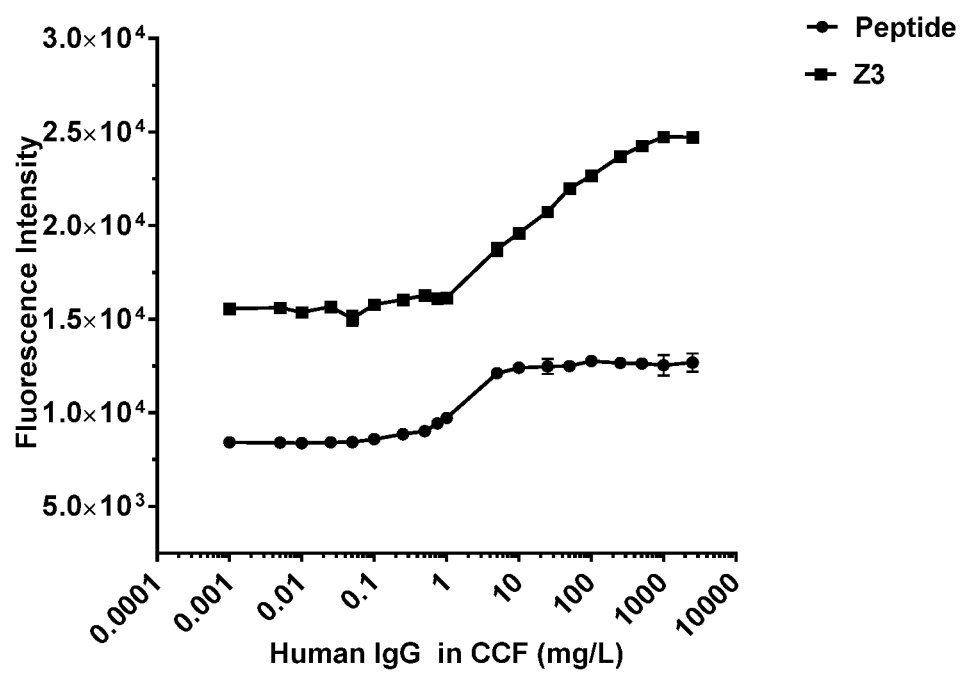
Figure 15A:
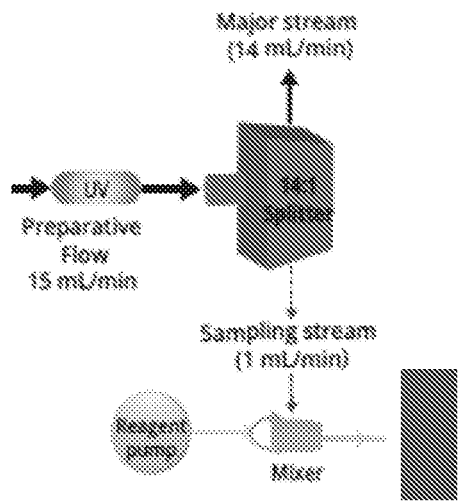
(FIG. 15A) Schematic for strategy for splitting the flow with post column flow splitter.
Figure 15B:
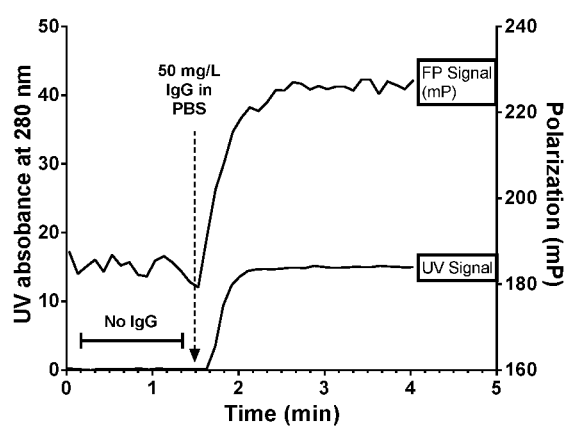
(FIG. 15B). Shift of fluorescence polarization of a three-domain analog of Protein A upon mixing with IgG in flow mode using a. The three-domain analog of Protein A (0.5 mL/min) was initially mixed with a small sampling pure buffer stream split from a stream which flows at high flow velocity (15 mL/min) followed by a stream (15 mL/min) containing IgG at 50 mg/L.
Figure 15C:
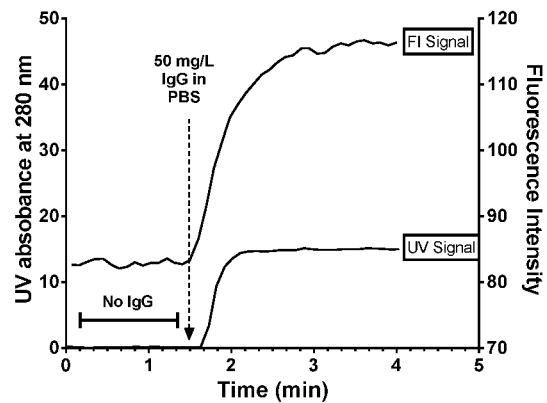
(FIG. 15C). Shift of fluorescence intensity of a three-domain analog of Protein A upon mixing with IgG in flow mode using a. The three-domain analog of Protein A (0.5 mL/min) was initially mixed with a small sampling pure buffer stream split from a stream (1 mL/min) which flows at high flow velocity (15 mL/min) followed by a stream (15 mL/min) containing IgG at 50 mg/L.
Figure 16:
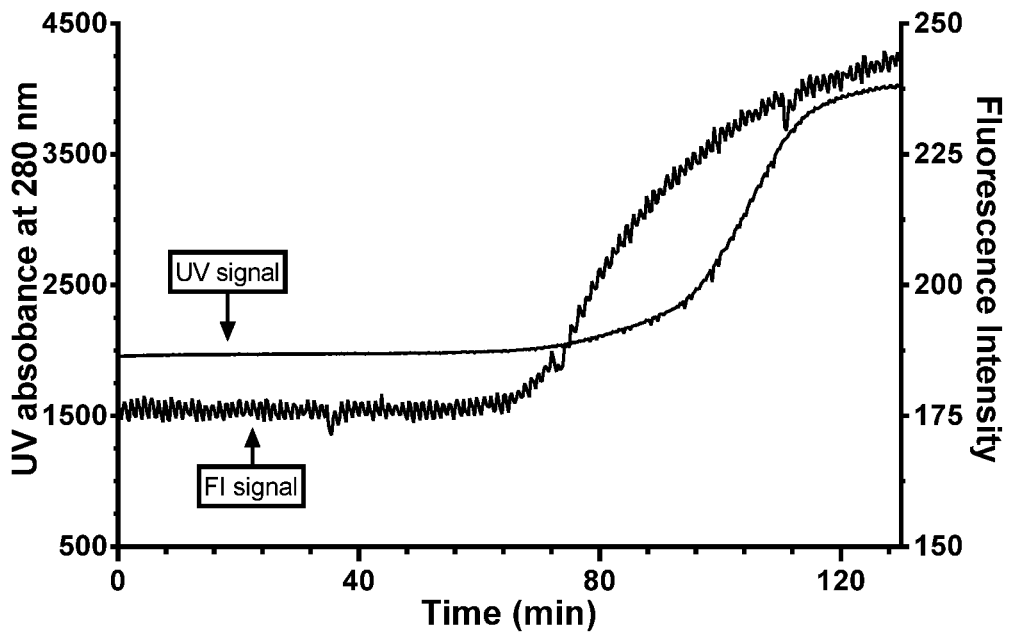
FIG. 16. Continuous detection human IgGs spiked in Murine-Ab-depleted hybridoma culture fluid (IMDM with 10% FBS) Protein A column breakthrough. High background absorbance at 280 nm due to cell culture fluid interferes with detection of the IgG breakthrough (at flow velocity of 80 cm/h) however increase in fluorescence intensity afforded by binding of three-domain analog of Protein A enables the detection of IgG in breakthrough.
Figure 17:
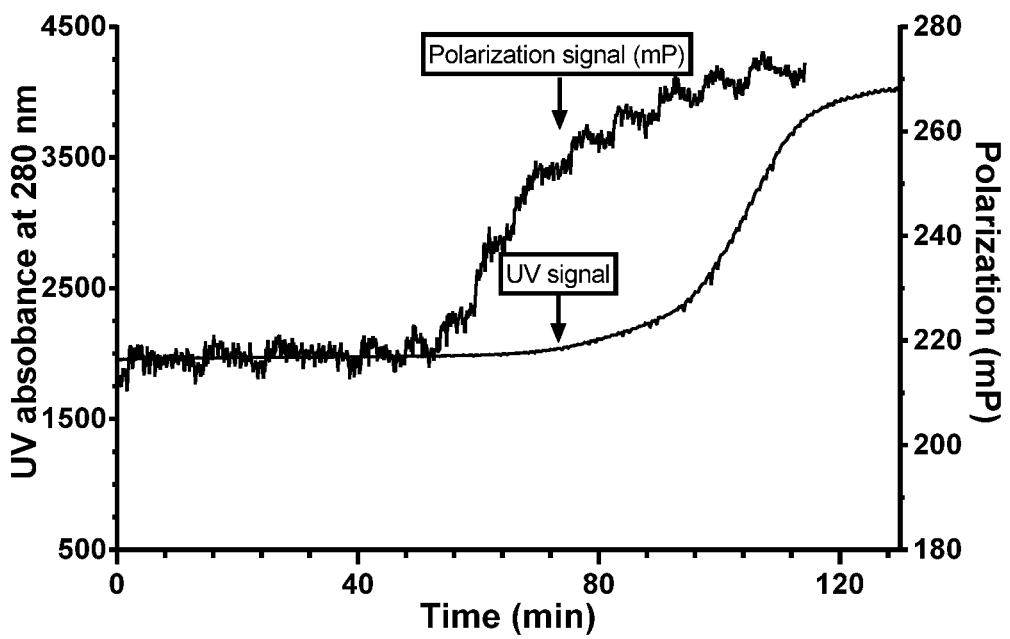
FIG. 17. Continuous detection human IgGs spiked in Murine-Ab-depleted hybridoma culture fluid (IMDM with 10% FBS) Protein A column breakthrough. High background absorbance at 280 nm due to cell culture fluid interferes with detection of the IgG breakthrough (at flow velocity of 80 cm/h) however increase in fluorescence polarization afforded by binding of three-domain analog of Protein A enables the detection of IgG in breakthrough.

In another example, the fluorescent signal is measured with total internal reflection fluorescence (TIRF) format in which the fluorescence labeled captured on the sensing surface is excited by evanescent wave generated by light that is total internal reflected at the sensing surface-water interface. The evanescent wave selectively excites fluorophores in the sub-micron depth adjacent to sensing surface-water interface. TIRF enables selective excitation of the fluorescent labeled element that is bridged to the capture element on the surface by the target protein, while non-bound molecules are not excited and do not fluoresce (FIG. 10). As the amount of target in sampling stream increases, it binds to the fluorescent labeled recognition element and is captured on the sensing surface, causing an increase in TIRF signal. The TIRF intensity is interpreted as the amount of target protein present.

Example 25: Monitoring of Target Protein in a Flow Stream Using Fluorescent Labeled Recognition Element Aided by Membrane Filtration In this example, a tangential membrane filtration module is fitted upstream to the fluorescence sensing cell. The cutoff for the membrane in the filtration module is selected in away that allows unbound or free fluorescent labeled recognition element to permeate through but retains bigger moieties. A high-velocity stream containing a target of interest is split using a fixed or variable or automated flow splitter with split ratios ranging from 10:1 to 20,000:1. The split sampling stream is combined with reagents containing fluorescent labeled recognition element which binds to the target protein. The fluorescent-labeled recognition element is mixed with the sampling stream using an active or passive mixer (such as T-connector) or inline mixer and flows to the filtration module. The carefully selected membrane cutoff allows unbound or free fluorescent labeled recognition element to permeate while retaining fluorescent labeled recognition element-target complex. The amount of fluorescent-labeled recognition element is optimized for desired sensitivity. When the sampling stream is devoid of the target, fluorescence remains low. As the amount of target in sampling stream increases, it binds to the fluorescent labeled recognition element. The fluorescence signal intensity increases with the amount of target in the sampling stream.

Example 26: Monitoring of Biologics in a Flow Stream During Aqueous Two-Phase Extraction Using Fluorescent Labeled Recognition Element Aqueous two-phase extraction (ATPE) is a viable alternative to chromatographic purification methods commonly used for purification of biologics. ATPE is a liquid-liquid extraction technique; the two phases are usually formed by either two hydrophilic polymers, or a polymer and salt when mixed above a certain concentration in water. The continuous counter-current ATPE can serve as a cost-effective purification process.

Figure 2:
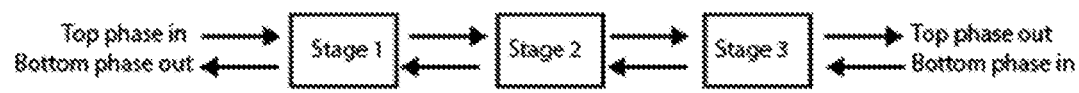
FIG. 2. Schematic for a continuous counter-current ATPE separation system

In this example, the feed containing a biological product, e.g., IgG mixed with top phase is passed through multistage extraction units (FIG. 2). The top phase outlet stream (raffinate) from stage 1 is fed to the next stage. The fresh bottom phase enters the extraction process at the Nth stage. The bottom phase travels in a direction opposite to the top phase (right to left). The concentration of IgG in raffinate after each stage decreases as it travels from stage 1 to stage N. The IgG concentration in raffinate stream after every stage or Nth stage is monitored by tapping a small sampling stream at high flow velocity. The bottom phase e.g. PEG can be modified by covalent affinity ligands for higher recovery yields. The bottom phase is enriched in IgG while the raffinate stream is depleted in IgG and is continuously monitored. The raffinate stream at high velocity is split using a fixed or variable or automated flow splitter with split ratios ranging from 10:1 to 20,000:1. The split sampling stream is combined with reagents containing fluorescent labeled protein A Z domain, in an active or passive mixer (such as T-connector) and flows to the flow cell fluorescence polarimeter. The amount of fluorescent-labeled protein A Z domain is optimized for desired sensitivity and response time. As the raffinate stream passes from stage 1 to stage N the IgG concentration decreases, the IgG in raffinate stream binds to the fluorescent labeled protein A Z domain to produce a shift in fluorescence polarization/anisotropy. During the ATPE process, when the raffinate is depleted of IgG, fluorescence polarization remains low. The shift in fluorescence polarization/anisotropy is proportional to the amount of IgG in the raffinate. When the shift in fluorescence polarization/anisotropy reaches a threshold, the ATPE process can be stopped.

Example 27: Monitoring of Recombinant Antibody Breakthrough During Affinity Chromatography Using Fluorescent Labeled Pseudo-Antibodies in a Competitive Format Molecular imprinting is based on the self-assembling of functional monomers around a template molecule. The complex is later polymerized in the presence of a crosslinker. Once the template is cleaved from the polymerized complex, a cavity remains that is complementary in shape to that of the template molecule. As a result, the new molecularly imprinted polymer (MIP) can bind molecules similar to the template molecule initially used and has been compared to naturally occurring antibodies. Recent advances in the polymerization processes have allowed the synthesis of MIPs as soluble nanometer-sized nanogels with sizes close to the size of natural antibodies.

In this example, the cell lysate is passed through the column and the effluent of chromatography column is monitored in real-time by tapping a small sampling stream at high flow velocity to minimize measurement delay time. The sampling stream is combined with reagents containing fluorescent labeled Fc fragment of IgG and custom designed MIP Fc binders in an active or passive mixer (such as T-connector) and flow to the flow cell fluorescence polarimeter. When the dynamic capacity of the column is reached, antibody begins flowing through the column without binding. The flow-through antibody displaces the Fc fragment from the MIP binder. The increase of free Fc fragment produces a shift in fluorescence polarization/anisotropy. The amount of shift in fluorescence polarization/anisotropy is proportional to the amount of antibody in the effluent stream. When the shift in fluorescence polarization/anisotropy reaches a threshold, the loading of cell lysate can be stopped or diverted to a different column in a multi-column format to prevent precious insulin going to waste and also to save processing time.

Example 28: Simultaneous Monitoring of Multiple Targets in Column Effluent During Affinity Chromatography Using Fluorescent Labeled Recognition Elements In this example, the cell lysate is passed through the column and the effluent of chromatography column is monitored in real-time by tapping a small sampling stream at high flow velocity to minimize measurement delay time. A high flow velocity stream containing targets of interest is split using a fixed or variable or automated flow splitter with split ratios ranging from 10:1 to 20,000:1. The split sampling stream is combined with reagents containing fluorescent labeled recognition elements (ligands) an active or passive mixer (such as T-connector) and flow to the flow cell fluorescence polarimeter. The fluorescent-labeled recognition elements selectively recognize their respective targets. The candidate fluorescent labels on the ligands are selected such that the emission wavelength of one of the fluorescent labels does not overlap with an excitation wavelength of the other fluorescent label. As the dynamic binding capacity of the column is reached, the targets begin flowing through the column without binding. The targets in the column effluent stream bind to the respective fluorescently labeled ligands. The binding of the targets to their respective ligands produces a shift in fluorescence polarization/anisotropy. The shift in fluorescence polarization/anisotropy is measured using an instrument equipped with fast switching excitation and/or emission filters. The amount of shift in fluorescence polarization/anisotropy for a particular ligand is proportional to the amount of the respective target in the effluent stream. When the shift in fluorescence polarization/anisotropy reaches a threshold, the loading of cell lysate can be stopped or diverted to a different column in a multi-column format to save processing time.

Example 29: Simultaneous Monitoring of Monoclonal Antibodies and Antibody Aggregates in Column Eluent During Affinity Chromatography Using Fluorescent Labeled Recognition Elements The protein A chromatography capture has become a platform for industrial monoclonal antibody purification. The captured antibodies are eluted from protein A resins by lowering the pH to 3.3. It's been previously reported that the low pH elution significantly increases the formation of antibody aggregates.

In this example, the clarified cell culture fluid is passed through the protein A column to capture the monoclonal antibodies. During the elution step, suitable buffer at low pH is passed through the column and the effluent of chromatography column is monitored in real-time by tapping a small sampling stream at high flow velocity to minimize measurement delay time. A high flow velocity stream is split using a fixed or variable or automated flow splitter with split ratios ranging from 10:1 to 20,000:1. The split sampling stream is combined with reagents containing two fluorescent labeled recognition elements (ligands) an active or passive mixer (such as T-connector) and flow to the flow cell fluorescence polarimeter. One of the fluorescent-labeled recognition elements (e.g., CIO) preferentially binds to antibody aggregates. The candidate fluorescent label for the aggregate binder is selected based on molecular weight of the said binder. As the low pH elution progresses the antibody and the aggregates begin flowing through the column. The antibody and the aggregates in the column effluent stream bind to the respective fluorescently labeled ligands. The binding of the targets to their respective ligands produces a shift in fluorescence polarization/anisotropy. The shift in fluorescence polarization/anisotropy is measured using an instrument equipped with fast switching excitation and/or emission filters. The amount of shift in fluorescence polarization/anisotropy for a particular ligand is proportional to the amount of the respective target in the effluent stream. When the shift in fluorescence polarization/anisotropy reaches a threshold, the elution peak pooling can be stopped or diverted to separate collection pool to avoid contamination of pooled product fractions with the aggregates.

Example 30: Monitoring of IgG1 Monoclonal Antibody in Column Effluent During Continuous Affinity Chromatography Using Fluorescent Labeled ZZ-Protein (Two Domains of Protein A)

Centrifuged tissue culture supernatant from a Chinese hamster ovary cell line expressing a recombinant IgG1 monoclonal antibody is flowed at 5 L per min into a 50 L column of agarose modified with recombinant protein A. One mL per minute of the fluid leaving the column is separated from the main stream, mixed in a Tee fitting with a syringe-pump-driven liquid stream containing recognition agent comprising two domains of protein A and a fluorescent label, and the mixture passed into a T format flow polarization anisotropy measurement device. A reduction in the anisotropy signal is interpreted as marking the beginning of antibody breakthrough from the column, and the flow leaving the column is switched into another column.

Example 31: Monitoring of a Recombinant Thrombolytic Enzyme in Column Effluent During Ion-Exchange Chromatography Using Fluorescent Labeled Aptamer Centrifuged and filtered tissue culture supernatant from an NS0 murine myeloma cell line expressing a recombinant thrombolytic enzyme of molecular mass 70 kDa is flowed at 1 L per min into a 40 L column of porous acrylic particles modified with negatively-charged sulfopropyl groups. 10 µL per sec of the fluid leaving the column is separated from the main stream and passed through a segment of a 30 kDa cutoff porous polymer membrane tube with pores too small to pass the enzyme, but large enough to pass smaller molecules. The tube is in contact with a bath of buffered liquid containing an aptamer which recognizes the enzyme and is labeled with fluorescein. Equilibration across the membrane removes competing intrinsic fluors, adjusts the pH to a selected value, and introduces the labeled aptamer into the flowing stream containing the enzyme. Some portion of the aptamer binds to the enzyme if present, producing a change in anisotropy. The mixture is passed into an L-format flow polarization anisotropy measurement device. A reduction in the anisotropy signal is interpreted as marking the beginning of enzyme breakthrough from the column and loading of the column is stopped.

Example 32: Monitoring of IgG1 Monoclonal Antibody in Column Effluent During Affinity Chromatography Using Fluorescent Labeled Protein L Centrifuged tissue culture supernatant from a Chinese hamster ovary cell line expressing a recombinant IgG1 monoclonal antibody is flowed at 30 mL per min into a 4 L column of agarose modified with recombinant protein L. One mL per minute of the fluid leaving the column is separated from the main stream, and mixed in a Tee fitting with an electrokinetic-pump-driven stream of a recognition agent comprising an anti-human-antibody scFv construct labeled with fluorescein. After passing through a length of nonporous tubing, the mixed stream is passed through a segment of low-diameter porous polymer membrane tube with pores too small to pass the antibody, but large enough to pass smaller molecules including the scFv. The tube is in contact with a bath of liquid containing suspended activated carbon which can adsorb the labeled scFv molecular recognition agent. The mixture is passed into a continuous fluorescence intensity measurement device set to fluorescein excitation and emission wavelengths. An increase in the fluorescence signal is interpreted as marking the beginning of antibody breakthrough from the column and loading of the column is stopped.

Example 33: Monitoring of Antibody Precipitation Process in Continuous Tubular Reactor Using Fluorescent Labeled Aptamer Monoclonal antibody precipitation has received renewed interest as a possible alternative to chromatographic purification. Precipitation is a cost-effective, high-yield and scalable step that holds enormous potential to reduce overall productions costs for antibody therapeutics. In this example, centrifuged tissue culture supernatant from a Chinese hamster ovary cell line expressing a recombinant IgG1 monoclonal antibody is mixed with precipitating stream. The precipitant stream usually contains a precipitant such as polyethylene glycol, ethanol, zinc chloride, a precipitant is used by itself or is combined with other precipitants to improve the antibody recovery. The stream containing the crude antibody extract is mixed with precipitant stream is passed through at tubular reactor fitted with static mixer. The precipitant stream is cooled to temperature suitable for the precipitant. One or more tubular reactors are connected in series to achieve desired level of antibody precipitate to maximize the recovery. The outlet of the tubular reactor is monitored in real-time by tapping a small sampling stream at high flow velocity. An outlet with flow rate 50 mL/min is split using a flow splitter attached to the outlet. A flow splitter with a split ratio of 50:1 results in flow rate 49.02 mL/min in the primary stream and 0.98 mL/min in the split stream. The split stream is equipped with a disposable filter cartridge such as membrane filter, depth filter to retain particulate matter which might interfere with the fluorescence polarimeter. The filtered split stream is combined with reagents containing fluorescent labeled aptamer in an active or passive mixer (such as T-connector) and the mixture flows to the flow cell fluorescence polarimeter. During the beginning of precipitation process, the concentration of soluble antibody is high. Thus fluorescence polarization remains high. Eventually, as the precipitation proceeds, the concentration of soluble antibody is reduced. The reduction is soluble antibody leads to shift in fluorescence polarization/anisotropy. The reduction in fluorescence polarization/anisotropy is proportional to the reduction in soluble antibody concentration. When the shift in fluorescence polarization/anisotropy is below a threshold, the precipitation process can be stopped or replenished with fresh feed containing antibody to save processing time.

Example 34: Monitoring Psychoactive Substances Abuse Using Fluorescent Labeled Recognition Elements In this example, the urinal wastewater from public urinals (e.g. toilets at festivals or in nightclubs or schools or On-Campus student Housing or dormitories) is transferred to sewage line using a waste water pumping system and the inlet stream is monitored in real-time by tapping a small sampling stream at high flow velocity. Finding data on illegal drug use is difficult, one of the ways of collecting such data is by sampling wastewater (including raw sewage). This could provide a real-time picture of a community's drug use, from urinals at schools, portable public urinals placed in areas in which target populations are expected to congregate or in which the use of new psychoactive substances is expected (e.g., at music festivals). The psychoactive substances Cocaine, amphetamine, methylenedioxymethamphetamine, methamphetamine, methadone, heroin and their metabolites are often found in the urinary excretion. The sampling stream is combined with reagents containing fluorescent labeled recognition elements (e.g., aptamers), in an active or passive mixer (such as T-connector) and flows to the flow cell fluorescence polarimeter. The amount of fluorescent-labeled recognition element is optimized for desired sensitivity and response time. When the urine or related sewage waste is devoid of psychoactive substances, fluorescence polarization remains low. When the psychoactive substance is present in sampling stream, it binds to the fluorescent labeled recognition element to produce a shift in fluorescence polarization/anisotropy. The shift in fluorescence polarization/anisotropy is proportional to the amount of psychoactive substance in urine.

Example 35: Monitoring of Glycosylation Type in Glycoprotein Therapeutic Modalities Using Fluorescent Labeled Recognition Elements A vast majority of the FDA approved therapeutic biologics are glycoproteins. Sialic acids are terminal, negatively charged monosaccharides present on many N- and O-glycans. Biopharmaceuticals frequently contain two main types of sialic acid; N-acetyl-neuraminic acid (NeuSAc) and N-glycolyl-neuraminic acid (Neu5Gc). NeuSAc is found in both human and non-human cells, whereas Neu5Gc not present on human glycoproteins and can be immunogenic.

In this example, the fluid containing product of interest is passed through a capture column suitable for capture of the product. During the elution step, suitable elution buffer is passed through the said column and the effluent of chromatography column is monitored in real-time by tapping a small sampling stream at high flow velocity to minimize measurement delay time. A high flow velocity stream is split using a fixed or variable or automated flow splitter with split ratios ranging from 10:1 to 20,000:1. The split sampling stream is combined with reagents containing two fluorescent labeled recognition elements (ligands) an active or passive mixer (such as T-connector) and flow to the flow cell fluorescence polarimeter. One of the fluorescent-labeled recognition elements (e.g., aptamer) specifically binds to product bearing Neu5Ac. The candidate fluorescent label for the fluorescent-labeled recognition element is selected based on molecular weight of the said fluorescent-labeled recognition element. Another fluorescent-labeled recognition element (e.g., peptide) specifically binds to product bearing Neu5Gc. As the elution progresses the product bearing Neu5Ac and/or Neu5Gc begin flowing through the column. The product variants bearing Neu5Ac or Neu5Gc present in the column effluent stream bind to the respective fluorescently labeled ligands. The binding of the targets to their respective ligands produces a shift in fluorescence polarization/anisotropy. The shift in fluorescence polarization/anisotropy is measured using an instrument equipped with fast switching excitation and/or emission filters. The amount of shift in fluorescence polarization/anisotropy for a particular ligand is proportional to the amount of the respective target in the effluent stream. The shift in fluorescence polarization/anisotropy is used to calculate absolute amounts of product bearing Neu5Gc and/or Neu5Ac and relative percentages thereof.

Example 36: Monitoring Psychoactive Substances Abuse Using Fluorescent Labeled Recognition Elements In this example, the wastewater from sewage system is transferred to sewage line using a suitable pumping system and the inlet stream is monitored in real-time by tapping a small sampling stream at high flow velocity. Finding data on community health is difficult, one of the ways of collecting such data is by sampling wastewater (including raw sewage). A collective community-wide basis by the monitoring of sewage for biomarkers of endogenous biochemical processes that reflect human health or disease, could provide a real-time picture of a community's health, from an area in which target populations are experiencing a health crisis. This approach can be referred to as Sewage Chemical-Information Mining. The biomarkers that can be monitored would be from their ability to reveal the overall status of health. The biomarkers that indicate underlying causes of disease, ill-health, dysfunction, stress, trauma, or injury, and the biomarkers that serve as positive (or prognostic) indicators of good health or wellness. The sampling stream from the sewage line is combined with reagents containing fluorescent labeled recognition element (e.g. peptide nucleic acid, PNA), in an active or passive mixer (such as T-connector) and flows to the flow cell fluorescence polarimeter. The amount of fluorescent-labeled recognition element is optimized for desired sensitivity and response time. When the urine or related sewage waste is devoid of biomarkers, fluorescence polarization remains low. When the biomarkers are present in sampling stream, it binds to the fluorescent labeled recognition element to produce a shift in fluorescence polarization/anisotropy. The shift in fluorescence polarization/anisotropy is proportional to the amount of biomarkers in urine or sewage.

Example 37: Monitoring Pathogens During Venipuncture for Blood Donation Using Fluorescent Labeled Recognition Elements Blood banks use many methods to try to prevent infections that can be transmitted by infected blood donation. Including testing donated blood for pathogens processing it for use for various therapeutic purposes.

In this example, the blood flowing through the blood draw tube is monitored in real-time by tapping a small sampling stream. Collecting real-time data on pathogens and other biomarkers in donors' blood is difficult, one of the ways of collecting such data is by un-interrupted sampling of the blood while its being collected during blood donation. The blood draw tube is equipped with sterile disposable splitting mechanism that splits the blood being drawn into major (collection) and minor (sampling) stream. The sampling stream is combined with reagents containing fluorescent labeled recognition elements, in an active or passive mixer (such as T-connector) and flows to the flow cell fluorescence polarimeter. The distal end of the reagent containing sampling stream is fitted with a sterile collection chamber at negative pressure. The amount of fluorescent-labeled recognition element is optimized for desired sensitivity and response time. When the blood is devoid of pathogens, fluorescence polarization remains low. When the pathogens are present in sampling stream, they bind to the fluorescent labeled recognition element to produce a shift in fluorescence polarization/anisotropy. The shift in fluorescence polarization/anisotropy is proportional to the amount of pathogens.

Example 38: Monitoring Pathogens During Aquaculture Using Fluorescent Labeled Recognition Elements Aquaculture is increasingly considered as an integral component in the search for global world food security and economic development. Major bacterial diseases affecting aquaculture can reduce the productivity of the aquaculture business.

In this example, the water from aquaculture system is transferred to recirculation line using a suitable pumping system and the inlet stream is monitored in real-time by tapping a small sampling stream at high flow velocity. Finding data on pathogens in aquaculture ponds is important to monitor overall health of the aquaculture organisms, one of the ways of collecting such data is by sampling aquaculture water. The sampling stream from the aquaculture water line is combined with reagents containing fluorescent labeled recognition element (e.g. peptide nucleic acid, PNA), in an active or passive mixer (such as T-connector) and flows to the flow cell fluorescence polarimeter. The amount of fluorescent-labeled recognition element is optimized for desired sensitivity and response time. When the water is devoid of pathogens, fluorescence polarization remains low. When the pathogens are present in sampling stream, it binds to the fluorescent labeled recognition element to produce a shift in fluorescence polarization/anisotropy. The shift in fluorescence polarization/anisotropy is proportional to the amount of pathogens in aquaculture water system.

Example 39: Monitoring Enrichment of Starting T-Cell Populations in CAR T Cell Manufacturing Cycle Using Fluorescent Labeled Recognition Elements T-cells engineered to express Chimeric Antigen Receptors (CARs) induce high rates of clinical responses in patients with hematologic malignancies and have demonstrated early indications of clinical activity in solid tumors. The manufacturing involves collection and enrichment of adequate starting T cell populations followed by ex vivo modification, activation, and expansion requiring sophisticated equipment and expertise. T-cell yields vary significantly based on patient, disease and collection factors. T-cell enrichment is accomplished through counter-flow centrifugal elutriation, which separates cells by size and density and maintains cell viability. In a typical counter-flow centrifugal elutriation process, Centrifugal force opposes force generated from a flow pump which pushes cells and other particles out of the chamber and into a collection vessel. Separations of cell types can be achieved varying flow and/or centrifugal force.

In this example, a buffer supply is attached to a spinning elutriation chamber spanned by a pump, pressure gauge, and sample injection inlet. Sample containing cells of interest is injected into reservoir and then pushed into elutriation chamber by buffer flow. The buffer flow is adjusted in way that promotes fractionation of cells which exit through the outlet valve of the said chamber. During the elutriation step, suitable elutriation buffer is passed through the said chamber spinning at suitable rpm and the outlet of chamber is monitored in real-time by tapping a small sampling stream at high flow velocity to minimize measurement delay time. A high flow velocity stream is split using a fixed or variable or automated flow splitter with split ratios ranging from 10:1 to 20,000:1. The split sampling stream is combined with reagents containing two or more fluorescent labeled recognition elements (ligands) an active or passive mixer (such as T-connector) and flow to the flow cell fluorescence polarimeter. One of the fluorescent-labeled recognition elements (e.g., aptamer) specifically binds to cell type of interest (T-Cell). The candidate fluorescent label for the fluorescent-labeled recognition element is selected based on molecular weight of the said fluorescent-labeled recognition element. Another fluorescent-labeled recognition element (e.g., peptide) specifically binds to respective cell type. As the elutriation progresses the cells begin flowing through the outlet of the chamber. The cell types present in outlet stream bind to the respective fluorescently labeled ligands. The binding of the targets to their respective ligands produces a shift in fluorescence polarization/anisotropy. The shift in fluorescence polarization/anisotropy is measured using an instrument equipped with fast switching excitation and/or emission filters. The amount of shift in fluorescence polarization/anisotropy for a particular ligand is proportional to the amount of the respective target cell type in the outlet stream. When the shift in fluorescence polarization/anisotropy reaches a threshold, the collection of cells can be stopped or diverted to separate collection pool to avoid contamination of pooled cell fraction.

Example 40: Monitoring Enrichment of Nanoparticles Using Fluorescent Labeled Recognition Elements Nanoparticle or nanomaterials enrichment can be accomplished through counter-flow centrifugal elutriation, which separates nanomaterial by size and density. In a typical counter-flow centrifugal elutriation process, centrifugal force opposes force generated from a flow pump which pushes nanoparticles out of the chamber and into a collection vessel. Separations of desired size nanoparticles can be achieved varying flow and/or centrifugal force.

In this example, a buffer supply is attached to a spinning elutriation chamber spanned by a pump, pressure gauge, and sample injection inlet. Sample containing nanoparticles of interest is injected into reservoir and then pushed into elutriation chamber by buffer flow. The buffer flow is adjusted in way that promotes fractionation of nanoparticles which exit through the outlet valve of the said chamber. During the elutriation step, suitable elutriation buffer is passed through the said chamber spinning at suitable rpm and the outlet of chamber is monitored in real-time by tapping a small sampling stream at high flow velocity to minimize measurement delay time. A high flow velocity stream is split using a fixed or variable or automated flow splitter with split ratios ranging from 10:1 to 20,000:1. The split sampling stream is combined with reagents containing two or more fluorescent labeled recognition elements (ligands) an active or passive mixer (such as T-connector) and flow to the flow cell fluorescence polarimeter. One of the fluorescent-labeled recognition elements (e.g., aptamer) specifically binds to nanoparticles of interest. The candidate fluorescent label for the fluorescent-labeled recognition element is selected based on molecular weight of the said fluorescent-labeled recognition element. Another fluorescent-labeled recognition element (e.g., peptide) specifically binds to respective nanomaterial. As the elutriation progresses the nanoparticles begin flowing through the outlet of the chamber. The nanoparticles present in outlet stream bind to the respective fluorescently labeled ligands. The binding of the targets to their respective ligands produces a shift in fluorescence polarization/anisotropy. The shift in fluorescence polarization/anisotropy is measured using an instrument equipped with fast switching excitation and/or emission filters. The amount of shift in fluorescence polarization/anisotropy for a particular ligand is proportional to the amount of the respective target cell type in the outlet stream. When the shift in fluorescence polarization/anisotropy reaches a threshold, the collection of nanoparticles can be stopped or diverted to separate collection pool to avoid contamination of pooled fraction.

Example 41: Monitoring of Antibody Using Fluorescent-Labeled Z3 Domain During Ultrafiltration/Diafiltration Ultrafiltration/Diafiltration (UF/DF) are commonly used processes during manufacturing of biologics such as monoclonal antibody. Therefore, monitoring UF/DF is desirable in development and manufacturing for monoclonal antibody.

In this example, the antibody containing stream is passed through a UF/DF membrane with desired cut-off selected with aim of retaining the antibody in retentate stream while allowing relatively smaller molecules to pass through in permeate stream. During the UF/DF step, suitable buffer at desired pH with or without excipients is passed through the membrane and the retentate stream from the membrane is monitored in real-time by tapping a small sampling stream at high flow velocity to minimize measurement delay time. A high flow velocity stream is split using a fixed or variable or automated flow splitter with split ratios ranging from 10:1 to 20,000:1. The split sampling stream is combined with reagents containing fluorescent labeled Z3 domain in an active or passive mixer (such as T-connector) and flow to the flow cell fluorescence intensity and/or polarimeter. The fluorescent-labeled Z3 domain binds to antibody. As the UF/DF process progresses the antibody and the aggregates begin flowing through the retentate stream. The antibody, aggregates and fragmented antibody products in the retentate stream bind to the fluorescently labeled Z3 domain. The binding of the targets to Z3 domain produces a shift in fluorescence intensity/polarization/anisotropy. The shift in fluorescence intensity/polarization/anisotropy is measured using an instrument equipped with fast switching excitation and/or emission filters. The amount of shift in fluorescence intensity/polarization/anisotropy for a Z3 ligand is proportional to the amount of the respective target in the retentate stream. When the shift in fluorescence intensity/polarization/anisotropy reaches a threshold, the UF/DF can be stopped.

Example 42: Monitoring Antibody of Using Fluorescent Labeled Z Domain During Diafiltration Diafiltration (DF) is commonly used process during manufacturing of biologics such as monoclonal antibody. DF are generally applied at least once during the production process. Therefore, monitoring DF is desirable in development and manufacturing for monoclonal antibody.

In this example, the antibody containing stream is pass through a DF device equipped with a membrane with desired cut-off selected with aim of retaining the antibody in retentate stream while allowing relatively smaller molecules to pass through in permeate stream. During the DF step, suitable buffer at desired pH with or without other excipients is transferred to antibody containing reservoir in periodic or continuous manner. The feed rate of DF buffer to the reservoir is adjusted in a way that allows the reservoir volume to be held constant. The antibody concentration in retentate stream is monitored in real-time by tapping a small sampling stream at high flow velocity to minimize measurement delay time. A high flow velocity stream is split using a fixed or variable or automated flow splitter with split ratios ranging from 10:1 to 20,000:1. The split sampling stream is combined with reagents containing fluorescent labeled Z domain in an active or passive mixer (such as T-connector) and flow to the flow cell fluorescence polarimeter. The fluorescent-labeled Z domain binds to antibody. As the DF process progresses the antibody concentration in retentate stream fluctuates depending on the feed rate of the DF buffer. The antibody in the retentate stream binds to the fluorescently labeled Z domain. The binding of the antibody to Z domain produces a shift in fluorescence intensity/polarization/anisotropy. The shift in fluorescence intensity/polarization/anisotropy is measured using an instrument equipped with fast switching excitation and/or emission filters. The amount of shift in fluorescence intensity/polarization/anisotropy for a Z domain is proportional to the amount of the respective antibody in the retentate stream. The correction for change in viscosity of the retentate can be introduced by measuring polarization of an additional non-interfering fluorescent dye molecule included in reagent stream. When the shift in fluorescence intensity/polarization/anisotropy of reaches or falls below a threshold, the DF buffer feed to the antibody reservoir can be resumed or stopped.

Example 43: Monitoring Protein PEGylation Using Fluorescent Labeled Recognition Element Conjugation of protein with polyethylene glycol (PEG) is a relatively common technique to reduce the renal clearance and increase circulation times as well as reducing immunogenicity. PEGylated drugs are available on the market, with a variety of PEG chain lengths, linkers and other properties. The typical production process consists of purifying the target protein and then performing batch conjugation on the purified protein.

In this example, the target protein is mixed with a reactive PEG derivative in a buffer at suitable pH, temperature and pressure. As the reaction proceeds the target protein is PEGylated and the molecular weight of the PEGylated form is higher than the non-PEGylated form. The progress of the PEGylation reaction is monitored in real-time by sampling the reactor contents from a recirculation loop. A high flow velocity stream is split using a fixed or variable or automated flow splitter with split ratios ranging from 10:1 to 20,000:1. The split sampling stream is combined with reagents containing fluorescent labeled recognition element in an active or passive mixer (such as T-connector) and flow to the flow cell fluorescence polarimeter. The fluorescent-labeled recognition element binds to target protein. The binding of the target protein to fluorescent labeled recognition element produces a shift in fluorescence polarization/anisotropy. The resultant increase in molecular weight of target protein due to PEGylation causes the shift in polarization to be higher than the non-PEGylated form. The shift in fluorescence polarization/anisotropy is measured using an instrument equipped with fast switching excitation and/or emission filters. The amount of shift in fluorescence polarization/anisotropy is proportional to the amount of the PEGylated target protein. When the shift in fluorescence polarization/anisotropy of reaches a threshold, the PEGylation can be stopped.

Example 44: Monitoring of Monoclonal Antibody in Breakthrough During Affinity Chromatography on MabSelect SuRe Using Fluorescent Labeled ZZZ-Domain MabSelect SuRe (GE Healthcare) is most commonly used antibody purification resin for chromatographic purification. The MabSelect SuRe ligand was developed by engineering one of the IgG-binding domains of protein A followed by its coupling to a agarose base matrix. The alkali-stabilized ligand allows cost-effective cleaning with 0.1-0.5 M NaOH over hundreds of purification cycles. During a typical chromatography capture step, a clarified harvested cell culture fluid containing recombinant IgG 10.0 g/L is applied to column at a flow rate of 300 mL/min or 19 L/h. Multiple flow splitters attached in series to column outlet split the outlet stream into primary and split streams. A flow splitter with a split ratio of 30:1 is followed by second flow splitter with a split ratio of 10:1 or vice versa. The high flow rate stream from the second flow splitter is reunited with primary stream from the first flow splitter to avoid loss of product. The split stream from second flow splitter is combined with reagents containing fluorescent labeled protein A ZZZ-domain (or Z3 domain) in an active or passive mixer (such as T-connector) and the mixture flows to the flow cell fluorescence polarimeter. In loading step of the affinity purification process, as the dynamic capacity of the column is reached, and antibody begins flowing through the column without binding. The flow-through of antibody binds to the fluorescent labeled ZZZ-domain to produce a shift in fluorescence polarization/anisotropy. The amount of shift in fluorescence polarization/anisotropy is proportional to the amount of antibody in the effluent stream. When the shift in fluorescence polarization/anisotropy reaches a threshold, the loading of feed can be stopped or diverted to the next column in a multi-column format.

Example 45: Monitoring of Host Cell Proteins During Purification of Biologics by Chromatography Using Fluorescent Labeled Labeled Recognition Element Chinese hamster ovary (CHO) cells are the primary choice for the industrial production of therapeutic proteins such as monoclonal antibodies (mAbs). Host cell proteins (HCPs) released from dead cells and secreted from viable cells accumulate extracellularly. Potential risks associated with specific HCPs include immunogenicity, adjuvant activity, proteolytic activity, and direct biological activity of potent molecules, therefore HCPs could impair product quality. HCPs like Lipoprotein lipase (LPL) can be copurified with the final biologic drug product such as a monoclonal antibody. LPL may degrade polysorbate 80 (PS-80) and polysorbate 20 (PS-20) in final product formulations due to the structural similarity between polysorbates and triglycerides.

In this example, monoclonal antibody-containing fluid is passed through a chromatography column and/or membrane. The chromatography process is operated in either capture or flow-through mode. During the purification process the effluent of chromatography column or membrane is monitored in real-time by tapping a small sampling stream at high flow velocity to minimize measurement delay time. A high flow velocity stream is split using a fixed or variable or automated flow splitter with split ratios ranging from 10:1 to 20,000:1. The split sampling stream is combined with reagents containing two or more fluorescent labeled recognition elements (ligands) an active or passive mixer (such as T-connector) and flow to the flow cell fluorescence polarimeter. The fluorescent-labeled recognition elements bind to the respective affinity partners. The candidate fluorescent label for the recognition elements is selected based on molecular weight of the said recognition element and the excitation/emission wavelengths for the fluorescent label. As the purification process progresses, the HCPs begin flowing through the effluent stream. The HCPs effluent stream bind to the respective fluorescently labeled ligands. The binding of the targets to their respective ligands produces a shift in fluorescence polarization/anisotropy. The shift in fluorescence polarization/anisotropy is measured using an instrument equipped with fast switching excitation and/or emission filters. The amount of shift in fluorescence polarization/anisotropy for a particular ligand is proportional to the amount of the respective target in the effluent stream. When the shift in fluorescence polarization/anisotropy reaches a threshold, the elution peak pooling can be stopped or diverted to separate collection pool or flagged for further analysis to avoid contamination of pooled product fractions.

Example 46: Cyclized Derivative of Protein A, G or L

In an embodiment, a target protein may be captured on a cyclized derivative of Protein A, G, or L, involving 1-10 domains, and optionally modified for base or protease resistance, and for easy immobilization through an amine or sulfhydryl. Cyclization may be achieved through Fusion of Z or protein A into backbone of cyclotides or other cyclic proteins/peptides.

Sortase transpeptidase enzyme from *Staphylococcus aureus* or other archaeal, prokaryotic and eukaryotic organism, Protein A or Z domain is fused to LPXTG either at Nt or Ct and a glycine on the other end. In the presence of sortase the LPXTG (or variants of this motif) can be ligated to the terminal glycine and protein is then cyclized.

Split-inteins: the C-intein followed by the C-extin is fused to the Nterminal of Protein A or Z domain whereas the N-extin followed by N-intein is fused to the Cterminal of Protein A or Z domain. A linker and/or affinity tag can be added to Nt or Ct of protein A or Z domain right before or after the N-extin or C-extin respectively.

Protein A or Z domain with C-terminal ester and free N terminal is incubated in presence of Subtiligase. This protein links the Ct ester to the free Nt by creating a peptide bond.

Protein is cyclized using SpyTag/SpyCatcher. SpyCatcher is fused at the N terminus and SpyTag at the C terminus. Cyclization can then take place in vivo.

Example 47: Detection of DNA in Effluent of Chromatography Column

DNA is detected in flow stream and/or effluent of chromatography column using fluorescent dye. Dye modulates the fluorescence intensity and/or fluorescence lifetime. Examples of such dyes are as follows but not limited to: propidium iodide, SYBR Gold, SYBR Green I and II, YO-PRO-1, TOTO-3, TO-PRO-3, PicoGreen, Ethidium bromide, DAPI, Hoechst stains, cyanine dyes, Eva Green.

Example 48: Detection of Viruses in Effluent of Chromatography Column

Virus (optionally boiled by passing through a heater or otherwise denatured using enzymes or chemically or physically denatured) is detected in a flow stream and/or effluent of chromatography column using fluorescent dye. Dye modulates the fluorescence intensity and/or fluorescence lifetime when contacted with components of the virus, especially nucleic acids. Examples of such dyes include but are not limited to: propidium iodide, SYBR Gold, SYBR Green I and II, YO-PRO-1, TOTO-3, TO-PRO-3, PicoGreen, Ethidium bromide, DAPI, Hoechst stains, cyanine dyes, Eva Green.

Example 49: Monitoring Enrichment of Starting T-Cell Populations in CAR T Cell Manufacturing Cycle Using Fluorescent Labeled Fab Fragment or the Whole Anti-CD3 Antibody T-cell enrichment is accomplished through counter-flow centrifugal elutriation, which separates cells by size and density and maintains cell viability. In a typical counter-flow centrifugal elutriation process, centrifugal force opposes force generated from a flow pump which pushes cells and other particles out of the chamber and into a collection vessel. Separations of cell types can be achieved varying flow and/or centrifugal force.

In this example, a buffer supply is attached to a spinning elutriation chamber spanned by a pump, pressure gauge, and sample injection inlet. Sample containing cells of interest is injected into reservoir and then pushed into elutriation chamber by buffer flow. The buffer flow is adjusted in way that promotes fractionation of cells which exit through the outlet valve of the said chamber. During the elutriation step, suitable elutriation buffer is passed through the said chamber spinning at suitable rpm and the outlet of chamber is monitored in real-time by tapping a small sampling stream at high flow velocity to minimize measurement delay time. A high flow velocity stream is split using a fixed or variable or automated flow splitter with split ratios ranging from 10:1 to 20,000:1. The split sampling stream is combined with reagents containing a fluorescent labeled whole anti-CD3 antibody or its Fab fragment in an active or passive mixer (such as T-connector) and flow to the flow cell fluorescence polarimeter. The fluorescent labeled whole anti-CD3 antibody or its Fab fragment specifically binds to CD3/T cell receptor. The candidate fluorescent label for the fluorescent-labeled recognition element is selected based on molecular weight of the said fluorescent-labeled recognition element. As the elutriation progresses the cells begin flowing through the outlet of the chamber. The cell types present in outlet stream bind to the respective fluorescently labeled ligands. The binding of the targets to their respective ligands produces a shift in fluorescence polarization/anisotropy. The shift in fluorescence polarization/anisotropy is measured using an instrument equipped with fast switching excitation and/or emission filters. The amount of shift in fluorescence polarization/anisotropy for a fluorescent labeled whole anti-CD3 antibody or its Fab fragment is proportional to the amount of the respective target cell type in the outlet stream. When the shift in fluorescence polarization/anisotropy reaches a threshold, the collection of cells can be stopped or diverted to separate collection pool to avoid contamination of pooled cell fraction.

Example 50: Monitoring Adeno-Associated Virus During Manufacturing Using Fluorescent-Labeled Fab Fragment or Whole Anti-AAV3 Antibody Recombinant adeno-associated virus (AAV) has demonstrated significant promise as a DNA-delivery vector to treat serious human diseases. Clinical studies using AAV vectors for the treatment of Alzheimer's disease, arthritis, Batten's disease, Canavan's disease, cystic fibrosis, hemophilia B, HIV infection, Leber's congenital amaurosis, Parkinson's disease, muscular dystrophy, prostate cancer and malignant melanoma have been initiated. Capto Core 700 column chromatography can be use in flow through purification of the AAV.

In this example, lysate of adenovirus-infected HEK293 human embryonic kidney cells is passed through a Capto Core 700 chromatography column. The chromatography process is operated in flow-through mode. During the purification process the effluent of chromatography column is monitored in real-time by tapping a small sampling stream at high flow velocity to minimize measurement delay time. A high flow velocity stream is split using a fixed or variable or automated flow splitter with split ratios ranging from 10:1 to 20,000:1. The split sampling stream is combined with reagents containing two fluorescent labeled recognition elements (ligands) an active or passive mixer (such as T-connector) and flow to the flow cell fluorescence polarimeter. One of the fluorescent-labeled recognition elements, the Fab fragment or the whole anti-AAV3 antibody binds to AAV. The candidate fluorescent label for the AAV binder is selected based on molecular weight of the said binder. As the purification process progresses the AAV and the contaminants begin flowing through the column. The AAV and the contaminants in the column effluent stream bind to the respective fluorescently labeled ligands. The binding of the targets to their respective ligands produces a shift in fluorescence polarization/anisotropy. The shift in fluorescence polarization/anisotropy is measured using an instrument equipped with fast switching excitation and/or emission filters. The amount of shift in fluorescence polarization/anisotropy for a particular ligand is proportional to the amount of the respective target in the effluent stream. When the shift in fluorescence polarization/anisotropy reaches a threshold, the flow-through collection can be stopped or diverted to separate collection pool to avoid contamination of pooled product fractions with the contaminants.

Example 51: Monitoring of Monoclonal Antibodies Column Effluent During Affinity Chromatography Using Multiple Fluorescent Labeled Recognition Elements In this example, the cell culture fluid containing IgG is passed through the protein A column and the effluent of chromatography column is monitored in real-time by tapping a small sampling stream at high flow velocity to minimize measurement delay time. A high flow velocity stream containing targets of interest is split using a fixed or variable or automated flow splitter with split ratios ranging from 10:1 to 20,000:1. The split sampling stream is combined with reagents containing two fluorescent labeled recognition elements (ligands) an active or passive mixer (such as T-connector) and flow to the flow cell fluorescence polarimeter. The fluorescent-labeled recognition elements selectively recognize IgG. One of the fluorescent-labeled recognition element (ZZZ) binds to the IgG with high affinity while the second fluorescent-labeled recognition element (Z) binds to the IgG with low affinity. The candidate fluorescent labels on the recognition elements are selected such that the emission wavelength of one of the fluorescent labels does not overlap with an excitation wavelength of the other fluorescent label. As the dynamic binding capacity of the column is reached, the IgG begin flowing through the column without binding. The IgG in the column effluent stream binds to the high affinity fluorescently labeled recognition element. The binding of the IgG to high affinity recognition element produces a shift in fluorescence intensity/polarization/anisotropy. As the IgG concentration in the effluent stream increases resultant shift from high affinity fluorescently labeled recognition element reaches to saturation. The increase in IgG concentration in the stream causes the low affinity fluorescently labeled recognition element to bind to IgG. The shift in fluorescence intensity/polarization/anisotropy for both fluorescently labeled recognition elements is measured using an instrument equipped with fast switching excitation and/or emission filters. The amount of shift in fluorescence polarization/anisotropy for a particular ligand is proportional to the amount of IgG in the effluent stream. When the shift in fluorescence polarization/anisotropy reaches a threshold, the loading of cell culture fluid can be stopped or diverted to a different column in a multi-column format to save processing time.

Example 52: Monitoring of Recombinant Antibody Breakthrough During Affinity Chromatography Using Fluorescent Labeled Affibody In this example, a cell lysate containing recombinant antibody fragment is passed through an affinity column (such as a protein A column) and the effluent of the chromatography column is monitored in real-time by tapping a small sampling stream at high flow velocity to minimize measurement delay time. A high flow velocity stream containing targets of interest is split using a fixed or variable or automated flow splitter with split ratios ranging from 10:1 to 20,000:1 or a sampling T. The split sampling stream is diverted to small/low capacity perfusive affinity column (protein A). The inlet and outlet of the perfusive column is monitored using UV/Vis flow cell. The difference between the inlet UV/Vis absorbance and outlet UV/Vis absorbance is used calculate the antibody concentration in primary column effluent.

In another example, the outlet of small/low capacity perfusive column is combined with reagents containing fluorescent labeled recognition elements (ligands) an active or passive mixer (such as T-connector) and flow to the flow cell fluorescence intensity/polarimeter. During the beginning of loading, when the dynamic capacity of the chromatography column is not reached, the antibody is not present in the column effluent and the split stream is devoid of antibody. Thus fluorescence intensity/polarization measured at the outlet of small/low capacity perfusive affinity column the remains low. When the dynamic capacity of the primary column is reached, antibody begins flowing through the column without binding. The flow-through antibody in split stream enters the perfusive column and breakthrough due to minimal capture by the said perfusive column. The antibody present in the outlet of small/low capacity perfusive column binds to the fluorescent labeled Z-domain to produce an increase in fluorescence intensity/polarization/anisotropy. The amount of shift in fluorescence intensity/polarization/anisotropy is reflective of the amount of antibody in the effluent stream of the primary column. When a shift in fluorescence polarization/anisotropy reaches a threshold, the loading of cell lysate can be stopped or diverted to a different column in a multi-column format to prevent precious antibody going to waste and to save processing time.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods, and in the steps or in the sequence of steps of the methods described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VI. REFERENCES

The following references, to the extent that they provide exemplary procedural or other details supplementary to those set forth herein, are specifically incorporated herein by reference.

Neurath et al., The Proteins, Academic Press, New York, 1979.
Godawat, Rahul, et al., *Biotechnology Journal* 7.12 (2012): 1496-1508.
Chmielowski, Rebecca A., et al., *Journal of Chromatography A* 1526 (2017): 58-69.
Choe, Weonu, Trishaladevi Durgannavar, and Sang Chung. *Materials* 9.12 (2016): 994.

What is claimed is:

1. A method of detecting the presence of a target analyte comprising
   (a) contacting a sample or a separated portion of said sample with a reporter reagent that produces an optically or electromagnetically detectable signal in the presence of the target analyte; and
   (b) determining the presence of said target analyte in said sample or said separated portion of said sample by measuring the optically or electromagnetically detectable signal, thereby detecting the presence of said target analyte, wherein
   (i) the sample is a first liquid stream is derived from a primary flow stream resulting from a separative process, or
   (ii) wherein the sample is formed from a separative process selected from the group consisting of chromatography, filtration/ultrafiltration, and precipitation/$ZnCl_2$ precipitation.

2. The method of claim 1, wherein the target analyte is a protein.

3. The method of claim 1, wherein the target analyte is a nucleic acid, a cell, a virus, a carbohydrate, or a lipid.

4. The method of claim 1, wherein the sample is a first liquid stream derived from a primary flow stream resulting from the separative process of step (i).

5. The method of claim 4, wherein the first liquid stream comprises less than 1% of the volumetric flow rate of the primary flow stream.

6. The method of claim 4, wherein the primary flow stream has a volumetric flow rate of more than about 1 mL per minute.

7. The method of claim 4, wherein the primary flow stream and the first liquid stream are split by a liquid flow splitter in a T format.

8. The method of claim 1, wherein the sample is formed from the separative process selected from the group consisting of chromatography, filtration/ultrafiltration, and precipitation/$ZnCl_2$ precipitation.

9. The method of claim 1, wherein the reporter reagent is introduced by mixing the sample prior to separation.

10. The method of claim 1, wherein the reporter reagent is introduced by mixing a separated portion of said sample with said reagent.

11. The method of claim 10, wherein the separated portion of said sample is mixed with a secondary liquid stream comprising the reporter reagent.

12. The method of claim 10, wherein the reporter reagent is introduced into the sample by dissolution or degradation of a solid matrix or transport through pores of a matrix, membrane or resin.

13. The method of claim 1, wherein the measuring takes place at a temperature of from about 0 to 60° C.

14. The method of claim 4, wherein the pH of the primary flow stream is lower than about pH 4.2.

15. The method of claim 11, wherein the mixture of the first liquid stream and the secondary liquid stream is adjusted by titration or addition of a buffering species to a pH greater than 5.0.

16. The method of claim 1, wherein the reporter reagent is associated with a particle, surface, or polymer.

17. The method of claim 1, wherein said sample is from a cell culture.

18. The method of claim 1, wherein said sample is from a reactor vessel, such as a fermentation reactor or a precipitation reactor.

19. A method of chromatographic purification of a target protein comprising:
    (a) introducing a sample comprising a target protein into a chromatographic column;
    (b) capturing the target protein on a chromatographic column matrix in said chromatographic column;
    (c) eluting matrix-captured target protein by change of pH, change of salt concentration, or change of polarity or hydrophobicity of the liquid flowing through the column;
    (d) introducing a reporter reagent into a portion of the liquid leaving the chromatographic column, wherein the reporter agent binds the target protein; and
    (e) measuring the concentration of the target protein in the liquid leaving the chromatographic column by detecting the reporter agent.

20. The method of claim 1, wherein the measuring takes place at a temperature of from about 0 to 30° C.

21. The method of claim 1, wherein the measuring takes place at a temperature of from about 0 to 60° C., or from about 0 to 30° C., or from about 3 to 25° C.

22. The method of claim 1, wherein the measuring takes place at a temperature of from about 3 to 25° C.

23. The method of claim 4, wherein the primary flow stream has a volumetric flow rate of more than about 50 mL per minute.

24. The method of claim 4, wherein the primary flow stream has a volumetric flow rate of more than about 1 liter per minute.

25. The method of claim 2, wherein the protein comprises an antibody or antibody fragment.

26. The method of claim 11, wherein the viscosity of the secondary liquid stream is greater than about 2 centipoise.

27. The method of claim 10, wherein the reporter reagent is introduced into the separated portion of said sample by dissolution or degradation of a solid matrix or transport through pores of a matrix or resin.

28. The method of claim 4, wherein the pH of the primary flow stream is adjusted by titration or addition of a buffering species to a pH greater than 5.0.

29. The method of claim 19, wherein the portion flow rate is less than 2% of the volumetric flow rate flowing through the column.

30. The method of claim 19, wherein the portion flow rate is at least 20 mL/min.

31. The method of claim 19, wherein measuring is made within 10, 20, 60, 300, or 2000 seconds of emergence of the portion from the chromatographic column.

32. The method of claim 19, in which the chromatographic column diameter is at least 40 cm.

* * * * *

SEQUENCE LISTING

```
<160> NUMBER OF SEQ ID NOS: 19

<210> SEQ ID NO 1
<211> LENGTH: 10
<212> TYPE: PRT
<213> ORGANISM: Artificial sequence
<220> FEATURE:
<223> OTHER INFORMATION: Synthetic peptide

<400> SEQUENCE: 1

Thr Trp Lys Thr Ser Arg Ile Ser Ile Phe
1               5                   10

<210> SEQ ID NO 2
<211> LENGTH: 10
<212> TYPE: PRT
<213> ORGANISM: Artificial sequence
<220> FEATURE:
<223> OTHER INFORMATION: Synthetic peptide

<400> SEQUENCE: 2

Phe Gly Arg Leu Val Ser Ser Ile Arg Tyr
1               5                   10

<210> SEQ ID NO 3
<211> LENGTH: 12
<212> TYPE: PRT
<213> ORGANISM: Artificial sequence
<220> FEATURE:
<223> OTHER INFORMATION: Synthetic peptide

<400> SEQUENCE: 3
```

```
Glu Pro Ile His Arg Ser Thr Leu Thr Ala Leu Leu
1               5                   10

<210> SEQ ID NO 4
<211> LENGTH: 4
<212> TYPE: PRT
<213> ORGANISM: Artificial sequence
<220> FEATURE:
<223> OTHER INFORMATION: Synthetic peptide

<400> SEQUENCE: 4

Ala Pro Ala Arg
1

<210> SEQ ID NO 5
<211> LENGTH: 6
<212> TYPE: PRT
<213> ORGANISM: Artificial sequence
<220> FEATURE:
<223> OTHER INFORMATION: Synthetic peptide

<400> SEQUENCE: 5

His Trp Arg Gly Trp Val
1               5

<210> SEQ ID NO 6
<211> LENGTH: 6
<212> TYPE: PRT
<213> ORGANISM: Artificial sequence
<220> FEATURE:
<223> OTHER INFORMATION: Synthetic peptide

<400> SEQUENCE: 6

His Tyr Phe Lys Phe Asp
1               5

<210> SEQ ID NO 7
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: Xaa = Citrulline

<400> SEQUENCE: 7

His Trp Xaa Gly Trp Val
1               5

<210> SEQ ID NO 8
<211> LENGTH: 4
<212> TYPE: PRT
<213> ORGANISM: Artificial sequence
<220> FEATURE:
<223> OTHER INFORMATION: Synthetic peptide

<400> SEQUENCE: 8

Asp Ala Ala Gly
1

<210> SEQ ID NO 9
<211> LENGTH: 6
<212> TYPE: PRT
<213> ORGANISM: Artificial sequence
<220> FEATURE:
<223> OTHER INFORMATION: Synthetic peptide
```

```
<400> SEQUENCE: 9

Arg Trp His Tyr Phe Lys
1               5

<210> SEQ ID NO 10
<211> LENGTH: 6
<212> TYPE: PRT
<213> ORGANISM: Artificial sequence
<220> FEATURE:
<223> OTHER INFORMATION: Synthetic peptide

<400> SEQUENCE: 10

Trp Phe Arg His Tyr Lys
1               5

<210> SEQ ID NO 11
<211> LENGTH: 8
<212> TYPE: PRT
<213> ORGANISM: Artificial sequence
<220> FEATURE:
<223> OTHER INFORMATION: Synthetic peptide

<400> SEQUENCE: 11

Asn Lys Phe Arg Gly Lys Tyr Lys
1               5

<210> SEQ ID NO 12
<211> LENGTH: 8
<212> TYPE: PRT
<213> ORGANISM: Artificial sequence
<220> FEATURE:
<223> OTHER INFORMATION: Synthetic peptide

<400> SEQUENCE: 12

Asn Ala Arg Lys Phe Tyr Lys Gly
1               5

<210> SEQ ID NO 13
<211> LENGTH: 8
<212> TYPE: PRT
<213> ORGANISM: Artificial sequence
<220> FEATURE:
<223> OTHER INFORMATION: Synthetic peptide

<400> SEQUENCE: 13

Phe Tyr Trp His Cys Leu Asp Glu
1               5

<210> SEQ ID NO 14
<211> LENGTH: 8
<212> TYPE: PRT
<213> ORGANISM: Artificial sequence
<220> FEATURE:
<223> OTHER INFORMATION: Synthetic peptide

<400> SEQUENCE: 14

Phe Tyr Cys His Trp Ala Leu Glu
1               5

<210> SEQ ID NO 15
<211> LENGTH: 8
<212> TYPE: PRT
<213> ORGANISM: Artificial sequence
<220> FEATURE:
<223> OTHER INFORMATION: Synthetic peptide
```

```
<400> SEQUENCE: 15

Phe Tyr Cys His Thr Ile Asp Glu
1               5

<210> SEQ ID NO 16
<211> LENGTH: 4
<212> TYPE: PRT
<213> ORGANISM: Artificial sequence
<220> FEATURE:
<223> OTHER INFORMATION: Synthetic peptide

<400> SEQUENCE: 16

Arg Arg Gly Trp
1

<210> SEQ ID NO 17
<211> LENGTH: 13
<212> TYPE: PRT
<213> ORGANISM: Artificial sequence
<220> FEATURE:
<223> OTHER INFORMATION: Synthetic peptide

<400> SEQUENCE: 17

Asp Cys Ala Trp His Leu Gly Glu Leu Val Trp Cys Thr
1               5                   10

<210> SEQ ID NO 18
<211> LENGTH: 174
<212> TYPE: DNA
<213> ORGANISM: Artificial sequence
<220> FEATURE:
<223> OTHER INFORMATION: Synthetic primer

<400> SEQUENCE: 18
tcgataacaa attcaacaaa gaacaacaaa acgcgttcta tgagatctta catttaccta      60
acttaaacga agaacaacga aacgccttca tccaaagttt aaaagatgac ccaagccaaa     120
gcgctaacct tttagcagaa gctaaaaagc taaatgatgc tcaagcaccg aaag          174

<210> SEQ ID NO 19
<211> LENGTH: 174
<212> TYPE: DNA
<213> ORGANISM: Artificial sequence
<220> FEATURE:
<223> OTHER INFORMATION: Synthetic primer

<400> SEQUENCE: 19
tcgactttcg gtgcttgagc atcatttagc tttttagctt ctgctaaaag gttagcgctt      60
tggcttgggt catcttttaa actttggatg aaggcgtttc gttgttcttc gtttaagtta    120
ggtaaatgta agatctcata gaacgcgttt tgttgttctt tgttgaattt gtta          174
```